US010610627B2

(12) United States Patent
Hayward

(10) Patent No.: US 10,610,627 B2
(45) Date of Patent: Apr. 7, 2020

(54) VENTRICULAR ASSIST DEVICE METHOD AND APPARATUS

(71) Applicant: St Vincent's Hospital Sydney Limited, Darlinghurst, New South Wales (AU)

(72) Inventor: Christopher Simon Hayward, New South Wales (AU)

(73) Assignee: ST. VINCENT'S HOSPITAL SYDNEY LIMITED (AU)

( * ) Notice: Subject to any disclaimer, the term of this patent is extended or adjusted under 35 U.S.C. 154(b) by 53 days.

(21) Appl. No.: 15/314,088

(22) PCT Filed: May 28, 2015

(86) PCT No.: PCT/AU2015/050288
§ 371 (c)(1),
(2) Date: Nov. 27, 2016

(87) PCT Pub. No.: WO2015/179921
PCT Pub. Date: Dec. 3, 2015

(65) Prior Publication Data
US 2017/0239407 A1   Aug. 24, 2017

(30) Foreign Application Priority Data
May 29, 2014   (AU) .................. 2014902046

(51) Int. Cl.
*A61M 1/10*   (2006.01)
*A61M 1/12*   (2006.01)
(52) U.S. Cl.
CPC .......... *A61M 1/1086* (2013.01); *A61M 1/101* (2013.01); *A61M 1/122* (2014.02);
(Continued)

(58) Field of Classification Search
CPC .... A61M 1/1086; A61M 1/122; A61M 1/101; A61M 2205/3334; A61M 2230/30; A61M 2205/50
See application file for complete search history.

(56) References Cited

U.S. PATENT DOCUMENTS 4,811,184 A   3/1989   Koninsky et al.
6,066,086 A   5/2000   Antaki et al.
(Continued)

FOREIGN PATENT DOCUMENTS

AU   2011201247 B2   3/2011
DE   102005030907 A1   6/2005
(Continued)

OTHER PUBLICATIONS

ISA/AU, International Search Report, Int'l Appln No. PCT/AU2015/050288, dated Oct. 8, 2015 (4 pages).
(Continued)

*Primary Examiner* — Mark Bockelman
(74) *Attorney, Agent, or Firm* — Fish IP Law, LLP

(57) ABSTRACT

Apparatus for use with a ventricular assist device that is assisting cardiac function of a biological subject, the apparatus including an electronic processing device that determines a flow rate of blood through the ventricular assist device, analyses the flow rate to determine a flow parameter value at least partially indicative of a change in the flow rate during diastole; and uses the flow parameter value to either derive at least one blood pressure parameter value at least partially indicative of a blood pressure in the biological subject or control the ventricular assist device.

20 Claims, 16 Drawing Sheets

(52) U.S. Cl.
CPC ... *A61M 1/1005* (2014.02); *A61M 2205/3334* (2013.01); *A61M 2205/50* (2013.01); *A61M 2230/30* (2013.01)

(56) References Cited

U.S. PATENT DOCUMENTS

| | | |
|---|---|---|
| 6,198,611 B1 | 3/2001 | Macbeth |
| 6,278,279 B1 | 8/2001 | Daun-Lindberg et al. |
| 6,504,692 B1 | 1/2003 | Macbeth et al. |
| 6,949,066 B2 | 9/2005 | Bearnson et al. |
| 8,506,470 B2 | 8/2013 | LaRose et al. |
| 2004/0152944 A1 | 8/2004 | Medvedev et al. |
| 2007/0188137 A1 | 8/2007 | Scheucher |
| 2008/0129307 A1 | 6/2008 | Yu et al. |
| 2010/0087742 A1 | 4/2010 | Bishop et al. |
| 2011/0210611 A1 | 9/2011 | Ledenev et al. |
| 2012/0081934 A1 | 4/2012 | Garrity et al. |
| 2012/0174961 A1 | 7/2012 | Larson et al. |
| 2014/0114202 A1 | 4/2014 | Hein et al. |
| 2015/0151032 A1 | 6/2015 | Voskoboynikov et al. |
| 2018/0228955 A1 | 8/2018 | Grannegger et al. |

FOREIGN PATENT DOCUMENTS

| | | |
|---|---|---|
| EP | 0428377 A3 | 11/1990 |
| EP | 2714388 B1 | 10/2015 |
| JP | 2004501678 | 1/2004 |
| JP | 2005514973 | 5/2005 |
| JP | 2009297174 | 12/2009 |
| JP | 2016533772 | 11/2016 |
| KR | 100703927 B1 | 10/2005 |
| WO | 03057280 A2 | 7/2003 |
| WO | WO2012/1000263 A2 | 7/2012 |
| WO | 2013184932 A1 | 12/2013 |
| WO | 2014015300 A1 | 1/2014 |
| WO | WO2014/015300 A1 | 1/2014 |
| WO | 2014044287 A1 | 3/2014 |

OTHER PUBLICATIONS

Corey J. Bishop, Nathan O. Mason; Abdallah G. Kfoury; Robert Lux; Sandi Stoker; Kenneth Horton, Stephen E. Clayson; Brad Rasmusson; Bruce B. Reid; A novel non-invasive method to assess aortic valve opening in HeartMate II left ventricular assist device patients using a modified Karhunen-Loève transformation; The Ournal of Heart and Lung Transplantaion; Jan. 2010; pp. 27-31; vol. 29, No. 1; Murray, Utah, US.

Marcus Granegger; Heinrich Schima; Daniel Zimpfer; Francesco Moscato; Assessment of Aortic Valve Opening During Rotary Blood Pump Support Using Pump Signals; Artificial Organs; 2014; pp. 290-297; vol. 38 (4); Artificial Organs; Center for Medical Physics and Biomedical Engineering, Medical University of Vienna; †Department of Cardiac Surgery, Medical University of Vienna; and ‡Ludwig-Boltzmann-Cluster for Cardiovascular Research, Vienna, Austria.

Hui-Lee Ooi; Siew-Cheok NG; Einly Lim; Robert F. Salamonsen; Alberto P. Avolio; Nigel H. Lovell; Robust Aortic Valve Non-Opening Detection for Different Cardiac Conditions; 2014; pp. 1-11; vol. 38(3):E57-E67; Artificial Organs; Department of biomedical Engineering, University of Malaya, Kuala Lumpur, Malaysia; †Department of Epidemiology and Preventive Medicine, Monash University, Melbourne; ‡Australian School of Advanced Medicine, Macquaries University and §Graduate School of Biomedical Engineering, University of New South Wales, Sydney, NSW, Australia.

Japanese Office Action with machine translation, Patent Application No. 2017-516933, dated Jul. 11, 2019 (5 pages).

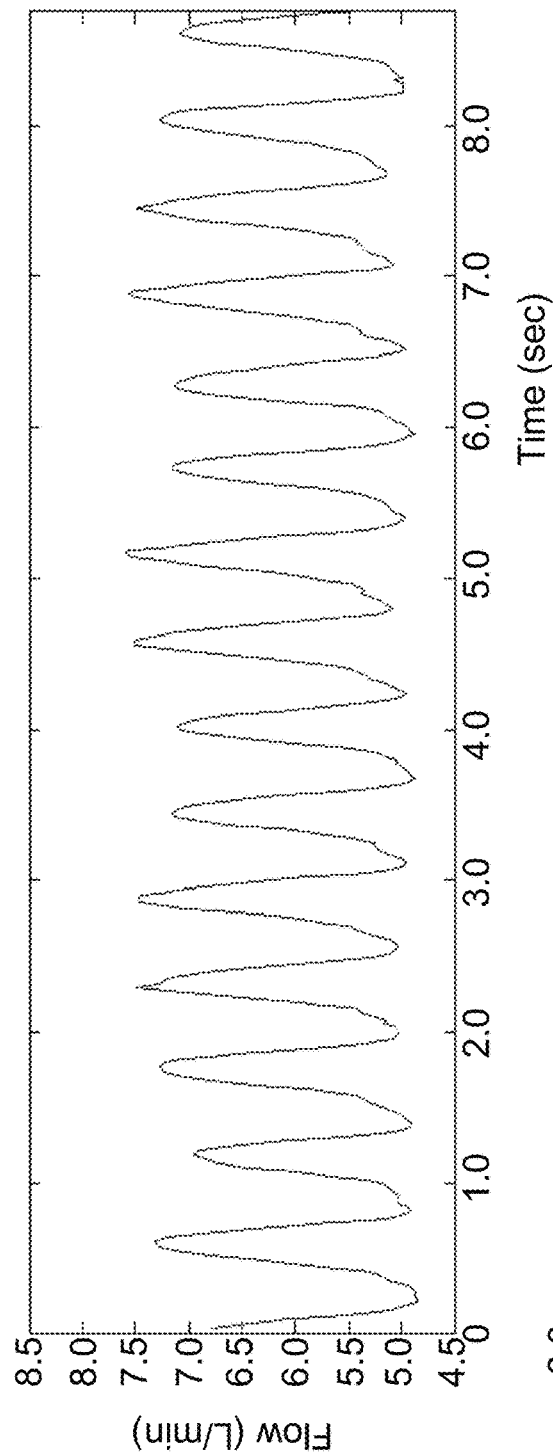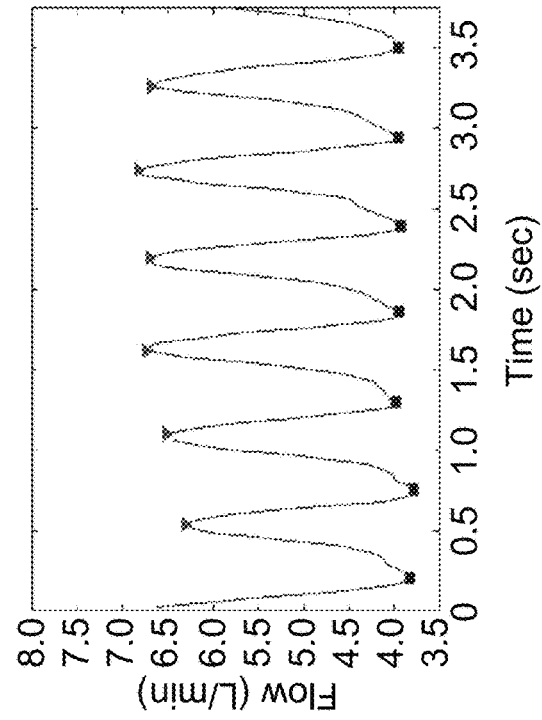

VENTRICULAR ASSIST DEVICE METHOD AND APPARATUS

BACKGROUND OF THE INVENTION

The present invention relates to a method and apparatus for use with a ventricular assist device that is assisting cardiac function of a biological subject, and to a method and apparatus for determining a blood pressure parameter value and/or controlling operation of the ventricular assist device.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Patients with impaired left ventricular function typically have low cardiac output and consequent poor exercise capacity. Some patients with particularly severe dysfunction require mechanical left ventricular assistance to "bridge" them to heart transplantation. Recent advances in mechanical assistance devices have shown 'third-generation' continuous flow pumps using a rotating impeller are both durable and reliable in providing cardiac output for patients with restoration of functional capacity and exercise capability to allow meaningful rehabilitation before transplantation.

Example third generation pumps from Ventrassist and HeartWare use an impeller rotating at a fixed speed (approximately 2000 rpm and 2700 rpm respectively) and rely on variations in preload and afterload to control pump output. Flow is related to head pressure, which equates to the difference between aortic and left ventricular pressure, with an increase in preload or decrease in afterload leading to an increase in output. Consequently, even at constant speed, flow through a cfLVAD increases with activity, mainly as a result of increased preload. However, this increase is modest in comparison to the physiological response to exercise. The weak preload and strong afterload sensitivities in cfLVADs relative to normal hearts mean that patients implanted with these devices are restricted in their ability to increase cardiac output with exercise when compared to normal subjects.

Thus, even though cfLVADs lead to improvements in exercise capacity, fatigue remains a limiting factor. The peak $VO_2$ (the maximum rate of oxygen consumption as measured during incremental exercise) achieved one to three months after pump insertion is only about half of the predicted value for normal subjects of the same age and gender and is significantly less than the predicted peak $VO_2$ demonstrated three months post-transplant. Thus, functional capacity is limited in the cfLVAD patient.

At present, no cfLVAD in clinical use has a physiological pump flow controller incorporated into the device. Research is underway to develop a controller that can automatically adjust pump flow in response to changes in the patient's haemodynamic state. In order to do this, inputs regarding pump and haemodynamic parameters are required. However, such information is difficult to obtain without implanting a sensor into the subject, which is impractical as a long term solution. In particular, implanted sensors create difficulties with thrombosis, malfunction, calibration and cost.

SUMMARY OF THE PRESENT INVENTION

In one broad form the invention seeks to provide apparatus for use with a ventricular assist device that is assisting cardiac function of a biological subject, the apparatus including an electronic processing device that:
a) determines a flow rate of blood through the ventricular assist device;
b) analyses the flow rate to determine a flow parameter value at least partially indicative of a change in the flow rate during diastole; and,
c) uses the flow parameter value to at least one of:
   i) derive at least one blood pressure parameter value at least partially indicative of a blood pressure in the biological subject; and
   ii) control the ventricular assist device.

Typically the flow parameter value is indicative of at least one of a flow rate gradient and a rate of change of flow rate during diastole.

Typically the electronic processing device:
a) compares a parameter value to at least one threshold, the parameter value being at least one of the flow parameter value and a blood pressure parameter value; and,
b) in response to results of the comparison, at least one of:
   i) selectively adjusts blood flow through the ventricular assist device; and.
   ii) selectively generates a notification.

Typically the threshold is at least one of:
a) indicative of a nominal range;
b) determined based on a parameter value determined from a sample population; and,
c) at least in part based on a parameter value previously determined for the subject.

Typically the ventricular assist device includes a rotating impeller, and wherein the electronic processing device controls blood flow through the ventricular assist device by causing a rate of rotation of the impeller to be adjusted.

Typically the electronic processing device:
a) determines the flow rate over at least one cardiac cycle; and,
b) analyses the flow rate to identify a period of the cardiac cycle corresponding to diastole;
c) determines the flow rate gradient during the diastole period; and,
d) determines the flow rate parameter value using the flow rate gradient.

Typically the electronic processing device:
a) analyses the flow rate over a plurality of cardiac cycles;
b) determines a mean flow rate gradient during diastole; and,
c) determines the flow rate parameter value using a mean flow rate gradient.

Typically the electronic processing device:
a) calculates flow rate maxima and minima for each of the plurality of cardiac cycles; and,
b) selectively excludes a cardiac cycle based on at least one of the respective flow rate maxima and minima of the cardiac cycle.

Typically the electronic processing device selectively excludes cardiac cycles corresponding to suction events.

Typically the electronic processing device:
a) calculates flow rate maxima and minima for each of the plurality of cardiac cycles; and,
b) determines a period of the cardiac cycle corresponding to diastole using the flow rate maxima and minima.

Typically the electronic processing device determines diastole as a period of the cardiac cycle from the flow rate minima to a proportion of the flow rate maxima.

Typically the proportion of the flow rate maxima is at least one of:

a) half of the flow rate maxima; and,
b) quarter of the flow rate maxima.

Typically the electronic processing device analyses the flow rate using waveform analysis.

Typically the electronic processing device at least one of:
a) records the flow parameter value;
b) displays a representation of the flow parameter value;
c) records a blood pressure parameter value; and,
d) displays a representation of the blood pressure parameter value.

Typically the at least one blood pressure parameter value is at least partially indicative of at least one of:
a) an intra-cardiac pressure;
b) an atrial pressure;
c) a ventricular filling pressure;
d) a pulmonary capillary wedge pressure;
e) a ventricular end diastole pressure; and,
f) a mean arterial pressure.

Typically the electronic processing device:
a) calculates a ventricular filling pressure using the flow parameter value;
b) determines a ventricular assist device power usage; and,
c) calculates a mean arterial pressure using the ventricular filling pressure and the ventricular assist device power usage.

Typically the electronic processing device is at least one of:
a) at least part of a ventricular assist device controller; and,
b) coupled to a ventricular assist device controller.

Typically the electronic processing device determines the blood flow rate at least one of:
a) in accordance with signals received from a sensor;
b) by receiving flow rate data from a ventricular assist device controller; and,
c) by calculating a flow rate based on rotation of a ventricular assist device impeller.

In one broad form the invention seeks to provide a method for use with a ventricular assist device that is assisting cardiac function of a biological subject, the method including:
a) determining a flow rate of blood through the ventricular assist device;
b) analysing the flow rate to determine a flow parameter value at least partially indicative of a change in the flow rate during diastole; and,
c) using the flow parameter value to at least one of:
i) derive at least one blood pressure parameter value at least partially indicative of a blood pressure in the biological subject; and,
ii) control the ventricular assist device.

In one broad form the invention seeks to provide apparatus for controlling a ventricular assist device, the apparatus including an electronic processing device that:
a) determines a flow rate of blood through the ventricular assist device;
b) analyses the flow rate to determine a flow parameter value at least partially indicative of a change in flow rate during diastole; and,
c) controls the ventricular assist device.

In one broad form the invention seeks to provide a method of controlling a ventricular assist device, the method including:
a) determining a flow rate of blood through the ventricular assist device;
b) analysing the flow rate to determine a flow parameter value at least partially indicative of a change in flow rate during diastole; and,
c) controlling the ventricular assist device.

In one broad form the invention seeks to provide apparatus for determining a blood pressure parameter value at least partially indicative of a blood pressure in the biological subject, the apparatus including an electronic processing device that:
a) determines a flow rate of blood through a ventricular assist device;
b) analyses the flow rate to determine a flow parameter value at least partially indicative of a change in flow rate during diastole; and,
c) uses the flow parameter value to determine the blood pressure parameter value.

In one broad form the invention seeks to provide a method of determining a blood pressure parameter value at least partially indicative of a blood pressure in the biological subject, the method including:
a) determining a flow rate of blood through a ventricular assist device;
b) analysing the flow rate to determine a flow parameter value at least partially indicative of a change in flow rate during diastole; and,
c) using the flow parameter value to determine the blood pressure parameter value.

BRIEF DESCRIPTION OF THE DRAWINGS

An example of the present invention will now be described with reference to the accompanying drawings, in which:—

FIG. 6A is a graph of an example of raw flow data from a ventricular assist device;

FIG. 6B is a graph of an example of raw flow data analysed to identify maxima and minima;

DETAILED DESCRIPTION OF THE PREFERRED EMBODIMENTS

Figure 1:
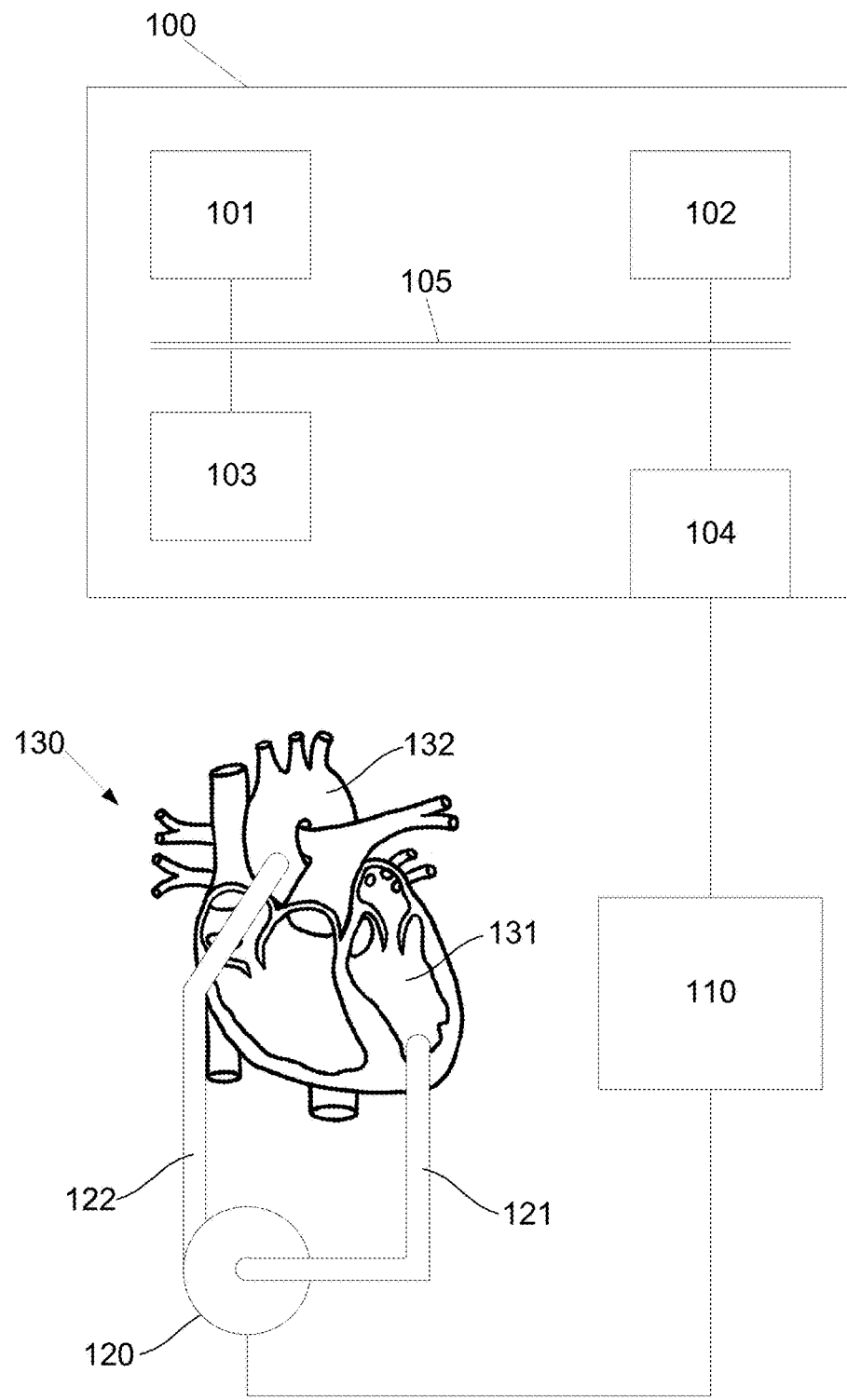
FIG. 1 is a schematic diagram of an example of apparatus for use with a ventricular assist device (VAD)

An example of an apparatus for use with a VAD will now be described with reference to FIG. 1.

In this example, the apparatus includes a processing system 100 that is coupled to a VAD 120, which is in turn connected to the heart 130 of a subject. In this example, the VAD is coupled via respective inlet and outlet cannulas 121, 122 to the left ventricle 131 and aorta 132, and is therefore functioning as a left ventricular assist device (LVAD), although this is not essential and similar techniques to those described can also be applied to right ventricular assist devices (RVADs) coupled to the right ventricle and pulmonary artery. The VAD is a continuous flow VAD (cfVAD) in which an impeller is continuously rotated within a cavity, to thereby pump blood from the ventricle into the aorta. The VAD 120 can be a standard VAD known in the art, such as a Heartware HVAD, Ventracor Ventrassist, or the like, and this will not therefore be described in further detail.

In this example, the processing system 100 is coupled to the VAD 120 via a controller 110, via a wired or wireless connection. The controller 110 operates to control the VAD and in particular control rotation of the impeller and optionally monitor operating characteristics of the VAD. This arrangement is not essential and alternatively the processing system 100 and controller 110 can be implemented as a single piece of hardware, although it will be appreciated that use of a separate processing system that interfaces with an existing controller can reduce regulatory requirements needed for implementation.

Figure 2:
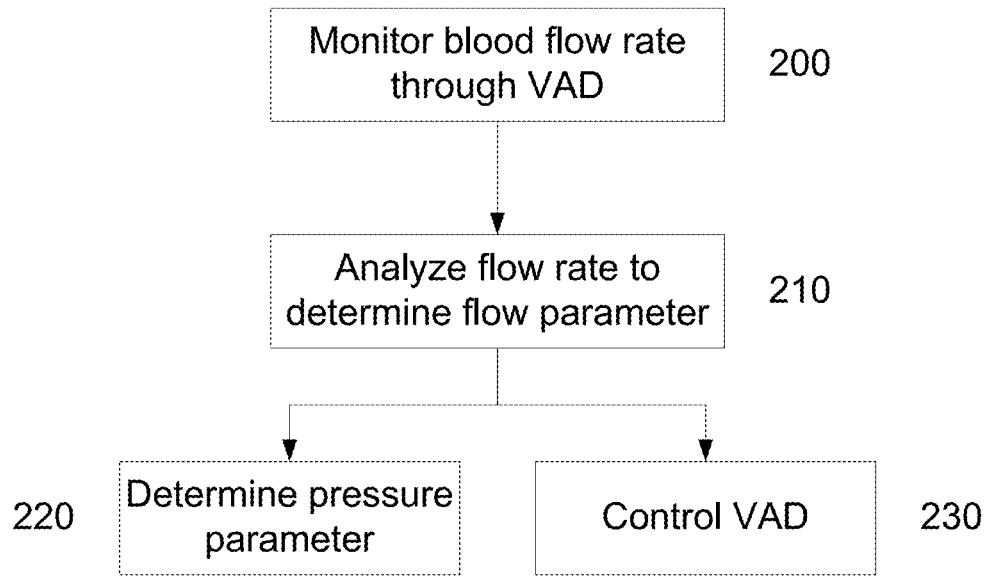
FIG. 2 is a flow chart of an example of a method for use with a VAD.

In use, the processing system 100 includes an electronic processing device, such as a microprocessor, that is adapted to determine information regarding the flow rate of blood through the VAD 120 and then use this to either control operation of the VAD, or determine blood pressure parameter values, as will now be described with reference to FIG. 2.

In this example, at step 200, the electronic processing device determines a flow rate of blood through the VAD 120. The flow rate can be determined in any suitable manner and can be obtained from sensors incorporated within the VAD 120, or alternatively could be derived from operating characteristics of the VAD 120, for example by monitoring rotation of the impeller as described for example in U.S. Pat. No. 8,506,470. The flow rate could be calculated by the electronic processing device or alternatively could be received as flow rate data from the controller 110, depending on the preferred implementation.

At step 210, the electronic processing device analyses the flow rate to determine a flow parameter value at least partially indicative of a change in flow rate during diastole. This can be achieved in any suitable manner, but typically involves identifying individual heart beats, analysing these to determine a portion of the heart beat corresponding to diastolic flow, and then calculating the flow parameter value. The flow parameter value can be of any appropriate form, but is typically the flow rate gradient corresponding to a rate of change of flow rate of blood through the VAD, as will be described in more detail below.

At step 220, the electronic processing device can use the flow parameter value to derive at least one blood pressure parameter value at least partially indicative of a blood pressure in the biological subject. In this regard, it has been determined that the rate of change in blood flow rate through the VAD during diastole is related to the blood pressure within the ventricle, and in particular, a ventricular filling pressure, such as the ventricular EDP (End Diastole Pressure). Accordingly, this allows the electronic processing device to derive information regarding blood pressure within the heart solely from information regarding the flow rate of blood through the VAD. Thus determination of the flow parameter value allows important physiological information to be derived without requiring the need for a sensor to be implanted within the patient.

In addition to being able to determine the ventricular filling pressure during diastole, this also allows additional parameters to be derived, such as the mean arterial pressure (MAP), as will be described in more detail below.

Additionally and/or alternatively, the parameter value, including either the flow parameter value or the pressure parameter value, can be used to control operation of the VAD. In particular, this can be used to adjust the pumping capacity of the VAD to accommodate changes in physiological status, for example to avoid suck-down events, provide additional pumping during exercise, or the like.

Accordingly, it will be appreciated that the above described method can be used to determine blood pressure parameter values that cannot otherwise be derived without the need to implant sensors within the heart, which is extremely undesirable, as well as allowing the operation of the VAD to be controlled to thereby optimize the assistance provided to the heart.

A number of further features will now be described.

In the above described example, the processing system 100 includes at least one microprocessor 101, a memory 102, an optional input/output device 103, such as a keyboard and/or display, and an external interface 104, interconnected via a bus 105 as shown. In this example the external interface 104 can be utilised for connecting the processing system 100 to the controller 110 and optionally to peripheral devices, such as the communications networks, databases, or the like. Although a single external interface 104 is shown, this is for the purpose of example only and in practice, multiple interfaces using various methods (eg. Ethernet, serial, USB, wireless or the like) may be provided.

In use, the microprocessor 101 executes instructions in the form of applications software stored in the memory 102 to allow flow rate data to be received from the controller 110 and used to calculate flow and blood pressure parameter values, as well as to generate control signals that can be transferred to the controller 110, allowing the operation of the VAD 120 to be controlled. The applications software may include one or more software modules, and may be executed in a suitable execution environment, such as an operating system environment, or the like.

Accordingly, it will be appreciated that the processing system 100 may be formed from any suitable processing system, such as a suitably programmed computer system, PC, web server, network server, or the like. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement.

Additionally and/or alternatively, the processing system 100 and controller 110 can be integrated into a single device. Thus, for example, the method of FIG. 2 could be performed using an existing heart pump controller modified to allow for the flow and blood pressure parameter values to be calculated. This could be achieved using a firmware and/or software upgrade or the like, as will be appreciated by persons skilled in the art.

As mentioned above, the flow parameter value is typically indicative of a rate of change in flow rate during diastole and can be calculated from the gradient of the flow rate against time.

To achieve this, the electronic processing device typically determines the flow rate over at least one cardiac cycle, analyses the flow rate to identify a period of the cardiac cycle corresponding to diastole, determines the flow rate gradient during the diastole period and determines the flow rate parameter value using the flow rate gradient. More typically, the electronic processing device analyses the flow rate over a plurality of cardiac cycles, determines a mean flow rate gradient during diastole and determines the flow rate parameter value using a mean flow rate gradient. Thus, the electronic processing device can determine a rolling average or mean of the flow rate gradient over a set number of cardiac cycles, allowing this to be used as the flow parameter value. This provides for a more stable parameter value and in particular avoids fluctuations in individual heart beats to unduly effect the determined flow parameter value and hence any derived blood pressure value.

The electronic processing device typically calculates flow rate maxima and minima for each of the plurality of cardiac cycles and selectively excludes a cardiac cycle based on at least one of the respective flow rate maxima and minima of the cardiac cycle. In particular, this allows the electronic processing device to selectively exclude cardiac cycles corresponding to suction events, which typically correspond to flow rate minima below the usual flow rate minima Additionally, the electronic processing device can use the flow rate maxima and minima to determine a period of the cardiac cycle corresponding to diastole, for example by defining diastole as a period of the cardiac cycle from the flow rate minima to a proportion of the flow rate maxima. The proportion could be a mid-point or a quarter of the flow rate maxima, however other proportions or time periods could be used, depending on the preferred implementation. For example, the end points used could be adjusted dynamically based on other measured parameters, such as heart rate or the like, thereby maximizing the length of time over which the gradient is calculated, whilst ensuring that the time period accurately corresponds to diastole and is not effected by onset of systole, plateaus in flow rate or the like. This provides a simple mechanism for identifying suction events, as well as to ascertain the period of the cardiac cycle corresponding to diastole, although it will be appreciated that other suitable techniques could be used, such as detecting diastole using changes in gradient.

The flow rate is generally analysed using waveform analysis as will be described in more detail below, although any suitable technique could be used.

Figure 3:
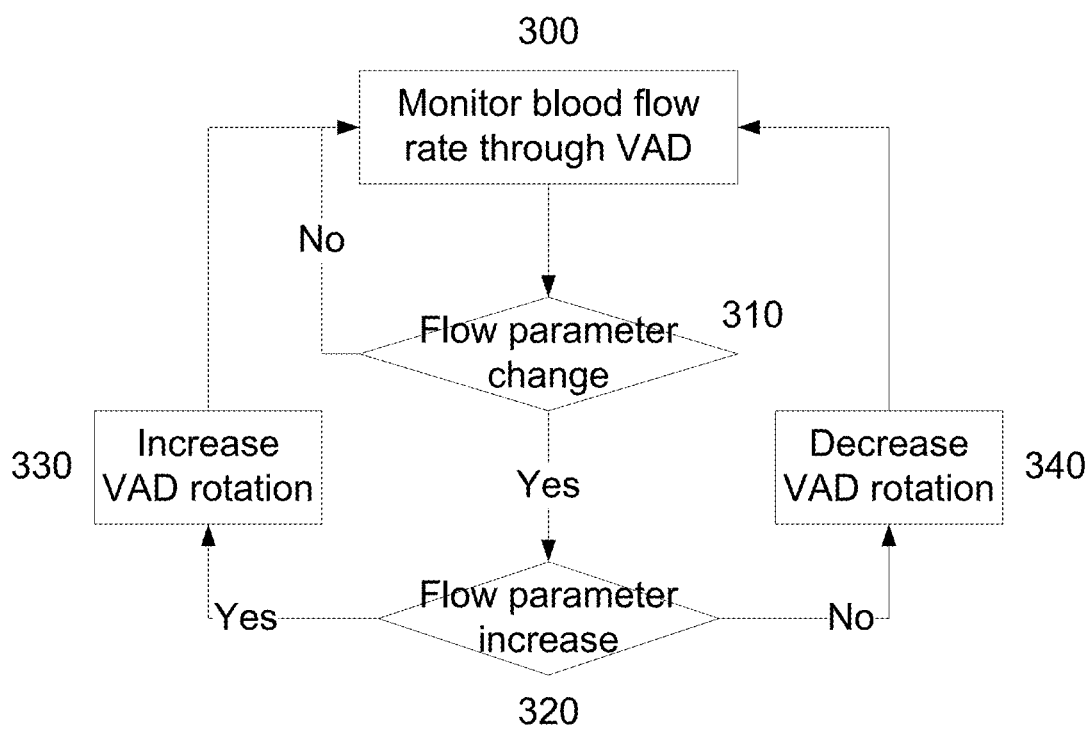
FIG. 3 is a flow chart of an example of a method of controlling a VAD.

The ventricular assist device generally includes a rotating impeller, in which case the electronic processing device controls blood flow through the ventricular assist device by causing a rate of rotation of the impeller to be adjusted. An example of this is shown in FIG. 3.

In this regard, at step 300 the electronic processing device monitors blood flow through the VAD. This could be performed in accordance with signals received from a sensor within the VAD, but more typically is achieved by receiving flow rate data from a ventricular assist device controller or calculating a flow rate based on rotation of a ventricular assist device impeller.

At step 310, the electronic processing device determines if there has been a change in the flow parameter value. If not, no action is required and the process returns to step 300. Otherwise, the process moves to step 320 to determine if the flow parameter value has increased or decreased.

In the event that the flow parameter value has increased, this is indicative of an increase in blood pressure within the ventricle and accordingly, the electronic processing device increases the speed of impeller rotation at step 330, to thereby increase the flow rate through the pump and hence reduce ventricular filling pressure. Conversely, if the flow parameter value has decreased, this is indicative of a decrease of blood pressure within the ventricle and accordingly the speed of impeller rotation is decreased at step 340. Accordingly, it will be appreciated that this process is effectively self-regulating, allowing the speed of impeller rotation to be continually adjusted to thereby ensure that blood pressure within the ventricle is maintained at a desired level. This can therefore automatically accommodate changes in blood pressure that arise from exercising or the like.

In the above example, the impeller speed is adjusted based on changes in the flow parameter value. It will be appreciated however that this could also be performed on the basis of the blood pressure parameter value derived from the flow parameter value as these are related by a defined mathematical relationship.

In the above example, even minor changes in pressure can result in adjustment of the impeller speed. However, as such continuous control may not be warranted, the electronic processing device can alternatively compare either the flow or blood pressure parameter value to at least one threshold and selectively adjusts blood flow through the ventricular assist device based on the results of the comparison. The threshold can be indicative of a nominal range, determined based on a parameter value determined from a sample population or at least in part based on a parameter value previously determined for the subject. Accordingly, in this example, a change in impeller speed would only be performed in the event that certain threshold boundaries are exceeded, such as a certain change in ventricular filling pressure or flow parameter from when the VAD speed was previously changed. Other suitable control mechanisms could be used, such as hysteresis control mechanisms, or the like.

A similar technique could be used to generate a notification, for example to indicate that there is a blood pressure problem, suction event or the like, which can be useful in monitoring patient welfare and operation of the VAD. The electronic processing device can also be adapted to record the flow parameter value, display a representation of the flow parameter value, record a blood pressure parameter value or display a representation of the blood pressure parameter value, allowing operation of the VAD and patient wellbeing to be recorded and subsequently reviewed. This can assist in identifying causes of adverse events, and hence taking action to mitigate these in future.

The blood pressure parameter value typically includes an intra-cardiac pressure, and in particular is usually a ventricular filling pressure, such as a ventricular EDP. It will be appreciated that this value is also typically related or similar to an atrial pressure and a pulmonary capillary wedge pressure (PCWP) during diastole, although this to some extent depends on the patient's heart function, and for example, whether the subject's aortic valve is open, as will be understood by persons skilled in the art. This can in turn be used to derive other pressure parameters including systemic pressures, such as a MAP, using information about heart function. In one particular example, the electronic processing device calculates a ventricular filing pressure using the flow parameter value, determines a ventricular assist device power usage and then calculates a mean arterial pressure using the ventricular pressure and the ventricular assist device power usage.

In this regard, the ventricular filling pressure is given by an equation of the form:

$$\text{EDP} = m \cdot dQ/dt + C \qquad (1)$$

where: EDP=ventricular end diastolic pressure
m=gradient constant
dQ/dt=flow rate gradient
C=constant The values of m and C are determined by measurements performed on a sample population. Based on collected data from one sample population, these were determined to be approximately m=4.778 and C=−14. However, it will be appreciated that these values may vary depending on a range of factors including the particular VAD used, heart function such as pump speed, viscosity, heart rate, ejection duration, and patient specific factors such as the patient's age, gender, ethnicity, or the like, and additional clinical data can be collected in this regard. Accordingly, it may be necessary to determine patient specific constant, or constants for specific categories of subject, as will be appreciated by persons skilled in the art.

In any event, the power used and pressure generated in the VAD are given by the equations:

$$W = V*I \qquad (2)$$

where: W=Power used
V=applied voltage
I=applied current $$\text{Pressure } (N/m^2) = \text{Power } (W)/\text{Flow } (m^3/s) \qquad (3)$$

$$\text{Pressure generated} = V*I/(Q*133.3) \qquad (4)$$

where: Q=flow rate
133.3 is a conversion factor into mmHg
The head pressure for the pump is given by:

$$\text{Head pressure} = \text{afterload pressure} - \text{preload pressure} \qquad (5)$$

Taking into account efficiency losses due to blood viscosity, and gradients due to outflow graft diameter, heat, friction, sound, turbulence, the mean arterial pressure whilst the aortic valve is closed is given by:

$$\text{MAP} = [(V*I/Q*133.3)*\eta] + (m \cdot dQ/dt + C) \qquad (6)$$

where: MAP=mean arterial pressure
η=pump efficiency losses

The pump efficiency losses are typically standard for each pump and accordingly, this allows the MAP to be calculated in real-time from the flow parameter. In this regard, when calculating MAP, this equation is typically only accurate whilst the aortic valve is closed, and accordingly, the process of determining the MAP will typically include determining whether the aortic valve is closed, which can be achieved using known techniques, and if so using equation (6) to calculate the instantaneous MAP. In the event that the aortic valve is open a different equation would be used, so over the entire cycle of a heartbeat, the MAP can be calculated using a combination of the two equations and information regarding the timing of the aortic valve opening and closing.

Accordingly, it will be appreciated that the above described arrangement allows blood pressure parameter values to be determined, whilst also allowing operation of the VAD to be controlled to accommodate changes in pressure caused by exercise or the like.

Figure 4:
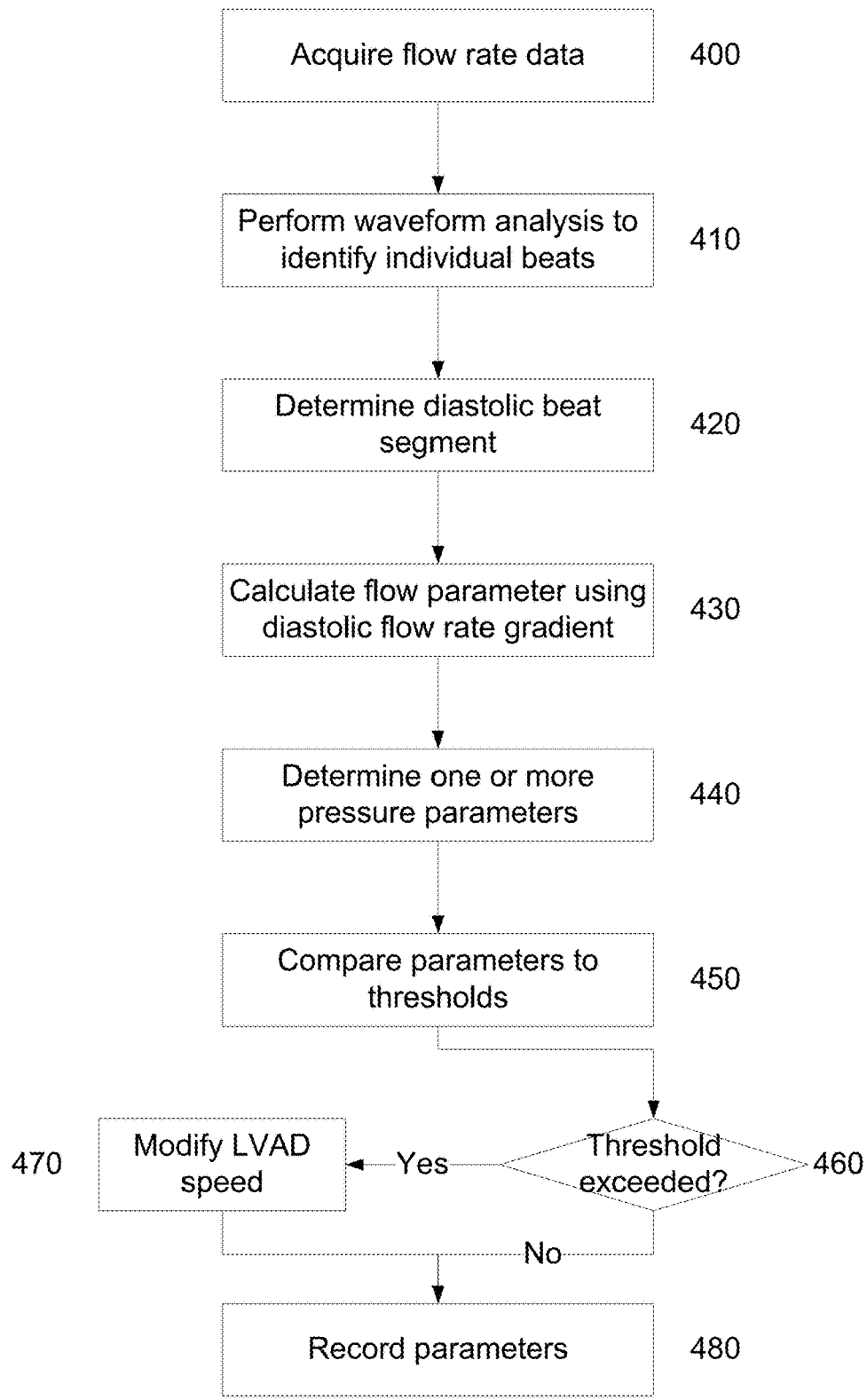
FIG. 4 is a flow chart of a second example of a method for use with a ventricular assist device.

A more detailed example of a method of operation will now be described with reference to FIG. 4.

In this example, at step 400, the electronic processing device acquires flow data indicative of blood flow through the VAD from the VAD controller. At step 410, the electronic processing device performs waveform analysis to identify separate cardiac cycles corresponding to individual heart beats. These are then examined at step 420 in order to identify the portion of the cardiac cycle corresponding to diastole, in a process that will be described in more detail with reference to FIG. 5.

At step 430, the flow parameter value is determined based on the gradient of the flow rate against time during the diastolic portion. It will be appreciated that this can be achieved using any suitable approach once the diastolic portion of the flow has been identified, for example by using a linear regression on the flow rate against time curve. One or more pressure parameter values are then determined at step 440, for example by using equations (1) to (6) above.

At step 450, the electronic processing device compares one or more of the parameters to respective thresholds to determine if the thresholds are exceeded. Thus, the flow parameter value can be compared to upper and lower limits representing values for which a change in pump speed is warranted. The thresholds could be based on fixed values, or alternatively could be relative, for example derived from baseline or other previous flow parameter values measured for the subject. For example, the threshold could be set at ±10% of the measured flow parameter value for the last flow rate change, with this being used to increase or decrease the pump speed as required. Thus, if the flow parameter value undergoes an increase of 10%, then the pump speed and hence throughput could be increased at step 470.

The flow and/or pressure parameter values could be recorded at step 480, for example as part of data logging to validate or monitor pump operation, and/or to form part of a patient record, allowing longitudinal tracking of blood pressure parameters. As a further step, at this point the thresholds used for the comparison could be updated, for example if the pump speed has been changed, otherwise the process returns to step 400 allowing the monitoring process to continue.

An example of a method for analysing the waveform will now be described with reference to FIG. 5.

In this example, the waveform analysis is used to determine characteristics such as heart rate, mean flow, mean maximum and minimum flow, and mean peak-to-trough amplitude, as well as detecting gradient of the flow waveform during diastole (diastolic dQ/dt) with a view to predicting the ventricular filling pressure.

In particular, at step 500 maxima and minima are identified in flow rate data corresponding to a number of heat beats. An example of the flow rate data is shown in FIG. 6A, with the maxima and minima being shown in FIG. 6B. At step 510, an average separation between the maxima and minima is calculated, with the mean flow rate being determined at step 520. It will be appreciated that this can be achieved using standard processing techniques and will not therefore be described in detail.

Figure 6C:
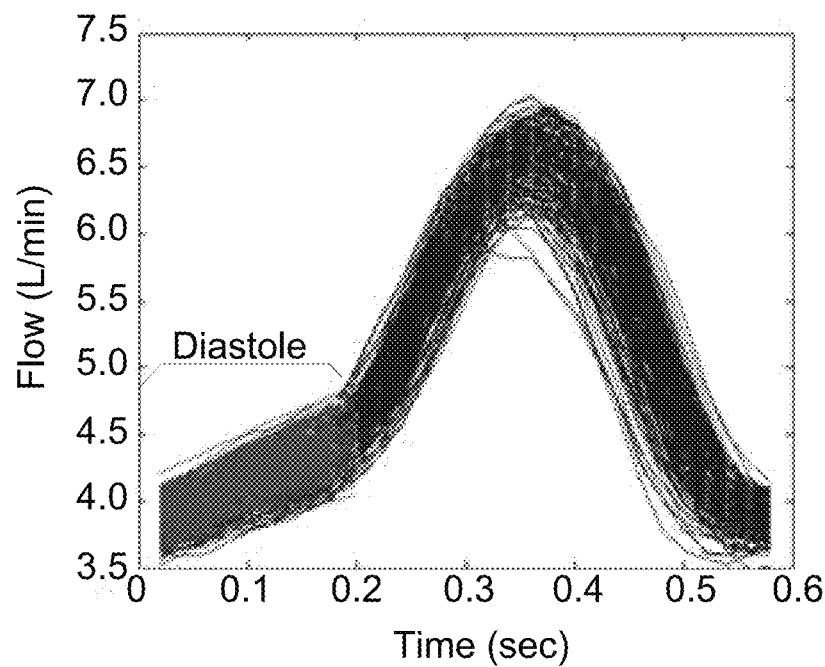
FIG. 6C is a graph of an example of flow data with individual beats delineated and overlaid with lines fitted to the diastolic period of each beat marked.

At step 530 suction events are removed, as will be described in more detail with reference to FIG. 7, as the suction events can unduly effect the calculation of flow rate. At step 540 mean maximum and minimum flow rates are calculated, with the difference between the means being determined at step 550. At step 560, the diastolic segment of each heat beat is determined using the difference between the means. In one example, diastole is defined as the period between the point of least flow and the point halfway to maximum flow, as shown in FIG. 6C, although other assessment criteria could be used.

At step 570, the gradient of the flow during diastole is determined, for example by fitting a line to the flow rate data using the method of least squares to determine the diastolic flow rate gradient dQ/dt. This can then be used to determine a mean flow rate gradient over a number of cycles at step 580, which represents the flow parameter value.

Figure 6D:
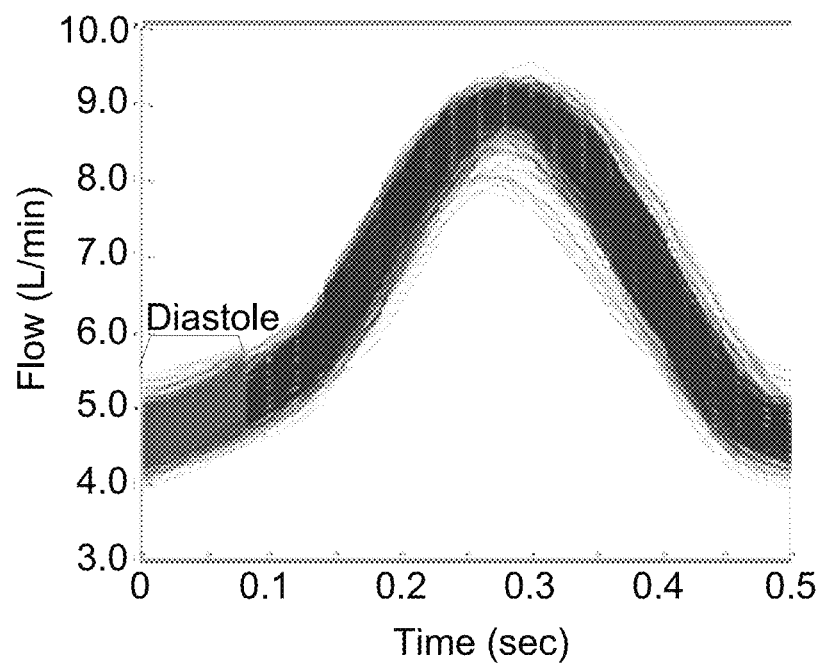
FIG. 6D is a graph of a second example of flow data with individual beats delineated and overlaid with lines fitted to the diastolic period of each beat marked.

However, as an alternative, the gradient during diastole could be measured between different end points, such as from a minimum flow to a point quarter way to maximum flow, as shown in FIG. 6D. In this example, the gradient is designated ndQ/dt, merely to distinguish this from the gradient dQ/dt shown in FIG. 6C. However, this is not intended to be limiting and in practice these measures can be used interchangeably as the gradient, and other measures of gradient could be used. Nevertheless, it has been shown that use of ndQ/dt can be more accurate than dQ/dt in some circumstances, as will be discussed in more detail below.

Figure 7:
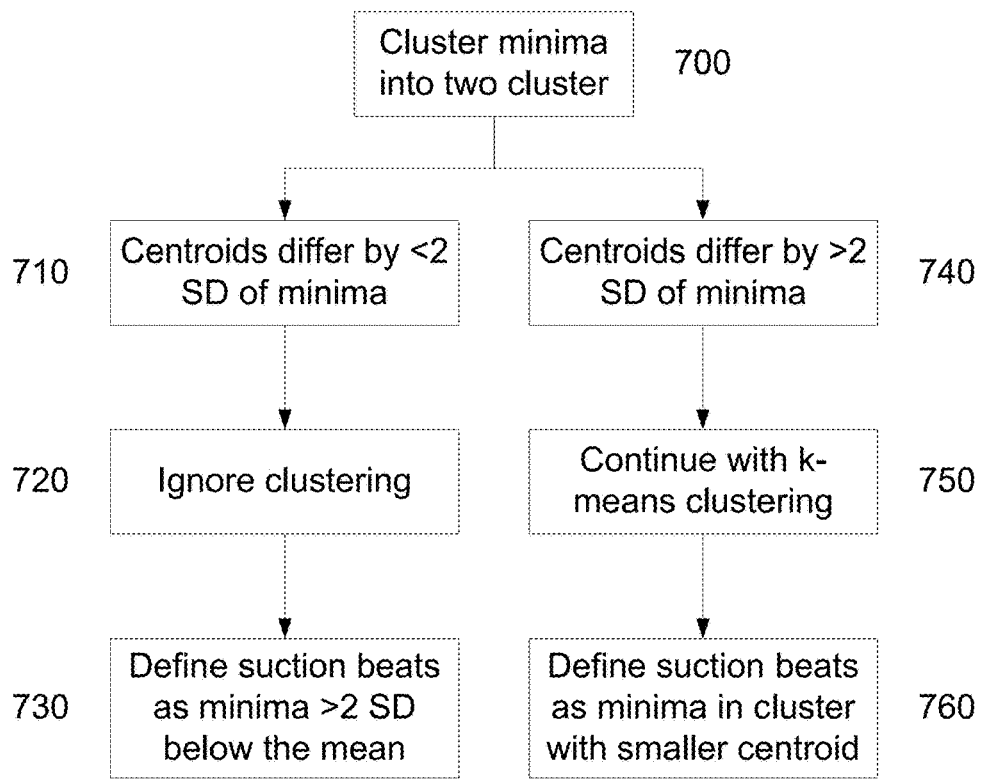
FIG. 7 is a flow chart of an example of a method of eliminating suction events.

The procedure used to analyse the flow waveforms to exclude sub-clinical suction events is shown in FIG. 7.

In this example, at step 700 minima are divided into two clusters. K-means clustering partitions observations into k clusters where each observation belongs to the cluster with the nearest mean or "centroid".

At step 710, it is determined if the centroids of each cluster are separated by less than two standard deviations, in which case at step 720 the clustering is ignored and suction beats are defined as those more than two standard deviations below the mean, at step 730. This process is used to eliminate occasional suction beats as shown in FIG. 8A.

Figures 8A, 8B:
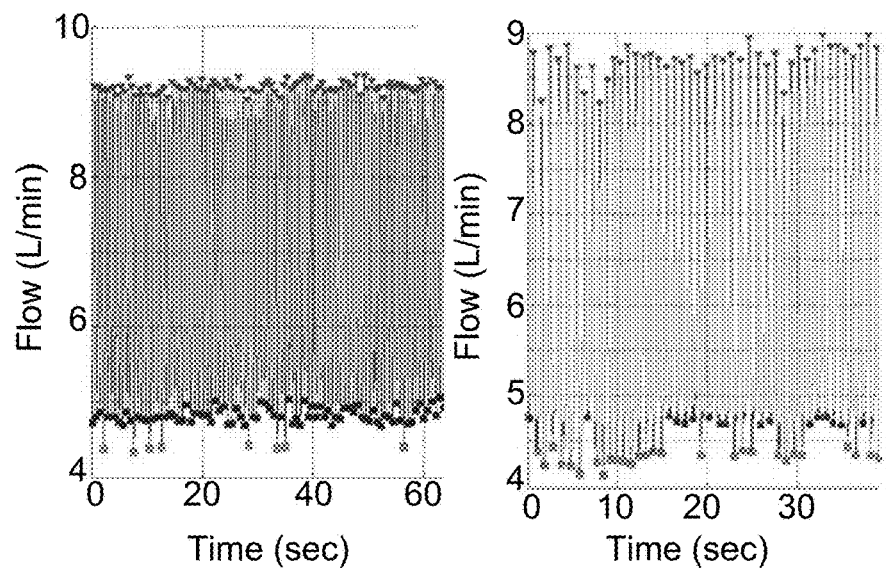
FIG. 8A is a graph of an example of isolated suction events.
FIG. 8B is a graph of an example of distinct populations of beats analysed using k-means clustering.

Alternatively, at step 740, it is determined if the centroids of each cluster are separated by more than two standard deviations, in which case clustering continues at step 750, with suction beats being defined as minima in the cluster with the smaller centroid, which is used to eliminate distinct populations of beats, as shown in FIG. 8B.

Experimental Study

In order to demonstrate the effectiveness of the flow parameter value as a measure of blood pressure and as well as the ability to be used in controlling a VAD, a study was performed on patients implanted with a continuous-flow HeartWare HVAD while undergoing routine right heart catherisation (RHC) as a part of transplant work-up. Each patient underwent RHC at rest followed by incremental exercise with the SwanGanz catheter in situ. Pump speed was up-titrated at rest to determine a maximum speed at which the pump could be safely operated. Patients then performed graded exercise at both baseline speed and the established maximum pump speed.

Patients were monitored throughout the study with the use of a continuous cardiac output monitor (Edwards Lifesciences Vigilance II Monitor), 12-lead ECG, transthoracic echocardiography (Acuson Cypress) and a computerised data acquisition system, which records the LVAD parameters speed, power and flow at a sampling rate of 50 Hz onto a portable computer hard drive.

Following administration of 2% xylocaine, RHC was performed under ultrasound guidance (SonoSite, Inc.) through the right or left internal jugular vein using a 7.5 French double transducer Swan-Ganz catheter (Edwards Lifesciences CCOmbo). Right atrial pressure (RAP), mean pulmonary arterial pressure (MPAP) and PCWP were measured, with PCWP being used as the ventricular filling pressure. Blood was sampled from the pulmonary artery for mixed venous oxygen saturation ($SvO_2$) calibration. Continuous cardiac output (CCO) was determined using the thermodilution technique. Heart rate was monitored using ECG while mean arterial pressure (MAP) was measured non-invasively with Doppler guided sphygmomanometry. LVAD parameters speed, power and flow were recorded from the HeartWare monitor. Left ventricular end systolic (LVESD) and diastolic dimensions (LVEDD), the opening of the aortic valve and the presence of any aortic or mitral regurgitation were also noted. These parameters were recorded at each stage of speed titration and exercise. Blood samples were also taken immediately pre- and post-exercise to determine B-type natriuretic peptide (BNP), lactate dehydrogenase (LDH) and lactate levels.

With the patient resting supine, all baseline haemodynamic, echocardiographic and pump parameters were recorded. With the patient still at rest, pump speed was then increased by 80 revolutions per minute (rpm) every two minutes. Up-titration was stopped at 320 rpm above baseline speed or in the event that LVEDD reduced to less than 80% of the resting value on echocardiography or flow exceeded 130% of baseline. Once a safe working maximum had been established, pump speed was reduced back to baseline in 80 rpm increments. Pump speed was maintained at baseline for a minimum of five minutes to allow for re-equilibration before proceeding with the exercise protocol.

Patients performed graded exercise on a supine bicycle ergometer (Lode B.Y. Medical Technology). Exercise workload was increased from zero watts in 15W increments to a peak of 60W or until exhaustion with patients pedalling at a cadence of 50 rpm. Light exercise, taken as 15W, was performed for one minute at baseline speed and then at maximum speed, as determined by the speed titration protocol. Workload was increased every minute thereafter with the patient exercising at maximum speed. Once peak exercise had been achieved, pump speed was dropped back down to baseline and the patient continued to exercise at peak workload for another minute. Parameters were recorded at each stage and in the recovery period following exercise. This protocol was chosen based on previous experience as it allowed patients to exercise across a range of workloads at both baseline and maximum speeds prior to reaching exhaustion.

Figure 5:
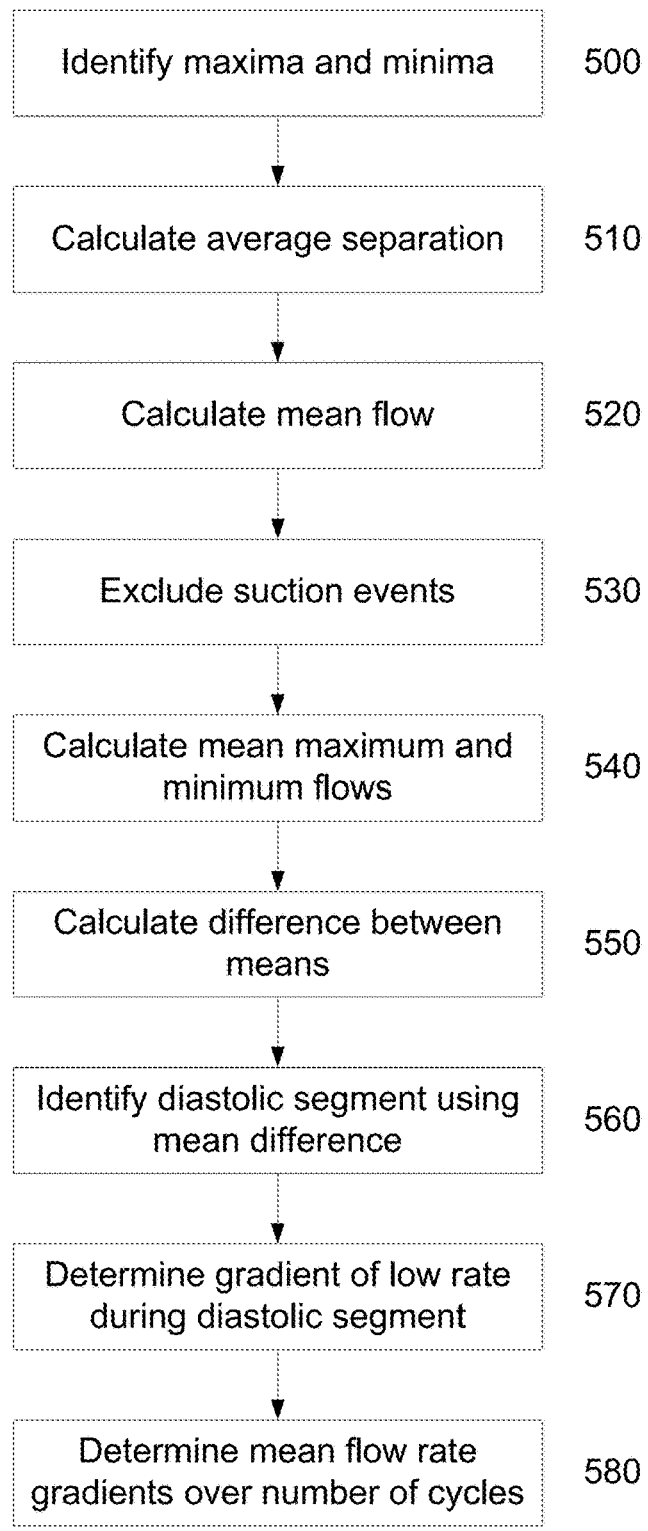
FIG. 5 is a flow chart of an example of a method of performing waveform analysis.

The process outlined in FIGS. 5 and 7 was performed in order to calculate the flow parameter values, with example flow against time waveforms being shown in FIGS. 9A to 9F. In each of these, flow rates over multiple different cardiac cycles are superimposed on a single graph, allowing comparison over multiple heart beats.

Figure 9A:
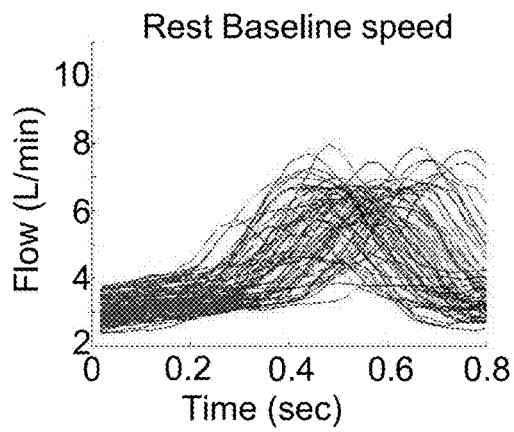
FIGS. 9A and 9B are graphs of example flow against time curves in a patient with atrial fibrillation and bigeminy, respectively.
Figure 9B:
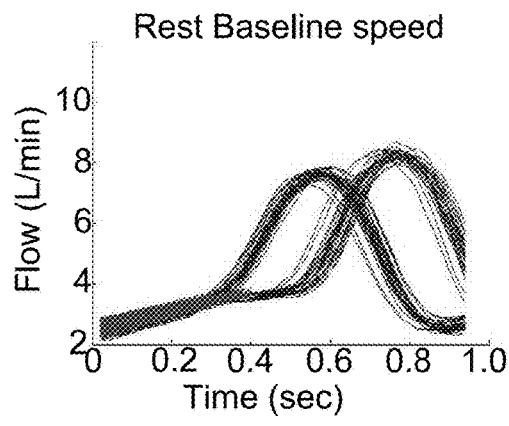

Example waveforms for patients with atrial fibrillation and bigeminy are shown in FIGS. 9A and 9B. These highlight how flow rate during systole varies significantly between different beats, resulting from different systolic ventricular pressure as a result of the fibrillation or bigeminy, in turn highlighting how the blood flow through the VAD is influenced by the patient's cardiac rhythm. It will be noted that the flow rate gradients during diastole remain relatively constant, highlighting that these values can be used to derive flow and blood pressure parameters even in patients suffering from these conditions, which typically would not be expected to have a major impact on ventricular filling pressure.

Figure 9C:
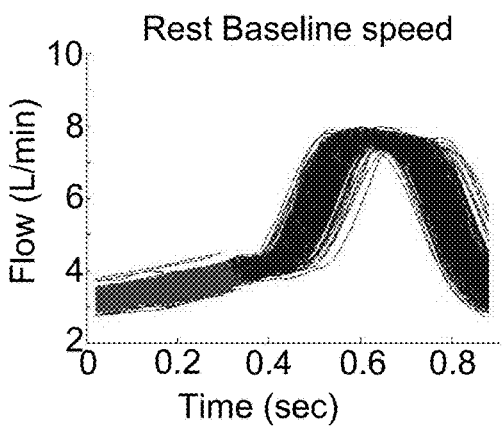
FIGS. 9C and 9D are graphs of example flow against time curves in a patient with a cfIVAD at baseline speed at rest and during peak exercise, respectively.
Figure 9D:
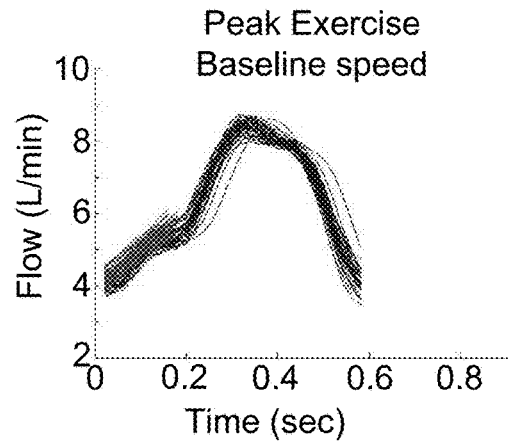
Figure 9E:
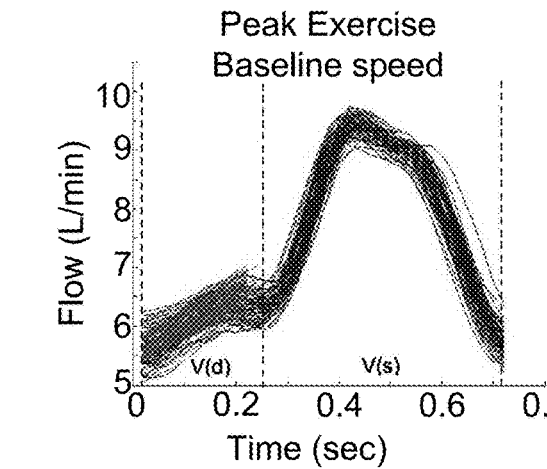
FIGS. 9E and 9F are graphs of example flow against time curves in a patient during peak exercise with an LVAD at baseline speed and maximum speed, respectively.
Figure 9F:
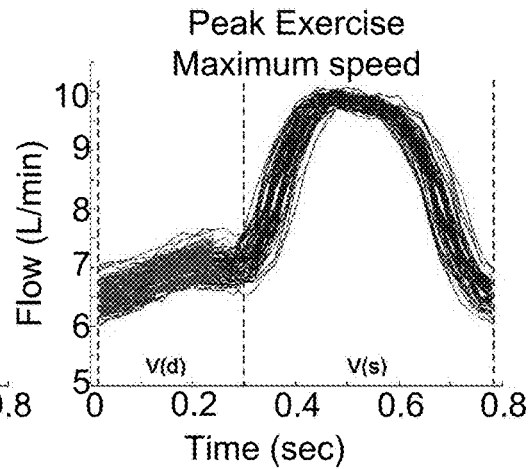

The examples of FIGS. 9C and 9D highlight how exercise causes an increase in the flow rate gradient during diastole, corresponding to an increase in ventricular filling pressure. FIGS. 9E and 9F show the effect of increasing pump speed during exercise, and in particular, that this can be used to reduce the flow rate gradient and hence ventricular filling pressure during diastole. Thus, this shows in broad terms how the flow rate gradient tracks expected ventricular filling pressure and that additionally an increase in pump speed is effect at counteracting the increased ventricular filling pressure resulting from exercise.

To further study the effects, statistical analysis was performed using SPSS version 21 (IBM, Chicago, IL., USA). Given the small sample size, normality could not be reliably assessed therefore analysis was conducted using non-parametric tests. The significance of differences in continuous outcomes between maximum and baseline speed performed at light and peak exercise were tested using the Related-Samples Wilcoxon Signed Rank Test.

The relationship between measured PCWP and diastolic flow rate gradient (dQ/dt) was analysed using linear mixed effects regression, controlling for heart rate, MAP and mean flow as a covariates. The mixed-effects model accounted for repeated measures within subjects by assuming each patient had their own unique response trajectory with a random intercept and slope. Parameters were estimated by maximum likelihood. Log-likelihood ratio tests were carried out to determine whether a random intercept model, a random slope model or a random intercept and slope model was necessary, however the tests were not significant and therefore analysis proceeded with stepwise multiple linear regression on the grounds of parsimony.

Assumption of linearity was checked by plotting PCWP against heart rate, MAP, mean flow and diastolic dQ/dt respectively. A histogram and normal probability plot were generated to assess normality of errors and the Durbin-Watson statistic satisfied the assumption that errors were independent. There was a large correlation between the predictor variables heart rate and diastolic dQ/dt (r=0.71, p<0.01), however, analysis of collinearity diagnostics suggested no issues with multicollinearity (VIF=2.2, tolerance=0.45).

Stepwise multiple linear regression of diastolic dQ/dt with PCWP, heart rate, MAP and mean flow as predictor variables was used to assess what variables contribute to this novel parameter and identify potential confounders.

Results are presented as median (range) or mean± standard deviation unless otherwise specified. A p-value of 0.05 was considered statistically significant.

Figure 10A:
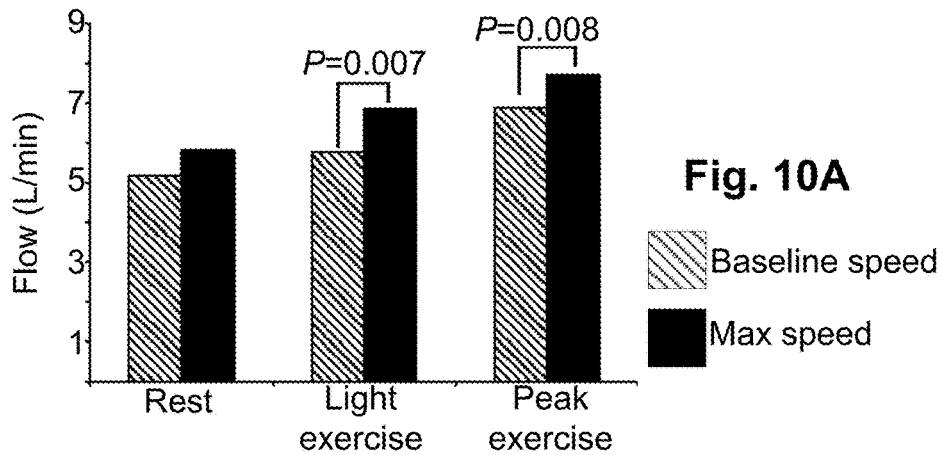
FIG. 10A is a graph showing an example of mean pump flow during rest, light exercise and peak exercise at baseline vs. maximum pump speed.

The results show that up-titration of pump speed during light exercise resulted in a significant increase in pump flow from 5.8±0.8 L/min at baseline to 6.8±0.8 L/min (p=0.007) at maximum speed, as shown in FIG. 10A, although there was no significant difference seen in CCO. MAP increased from 86 mmHg at baseline speed to 92 mmHg at maximum speed (p=0.04). Heart rate, RAP, MPAP, SPAP and SvO2 did not differ significantly between the two speeds. LVEDD and LVESD also remained unchanged. The aortic valve was opening in four of the nine patients at baseline speed and intermittently opening in one patient. All five of these patients had their aortic valve opening at maximum speed.

Figure 10B:
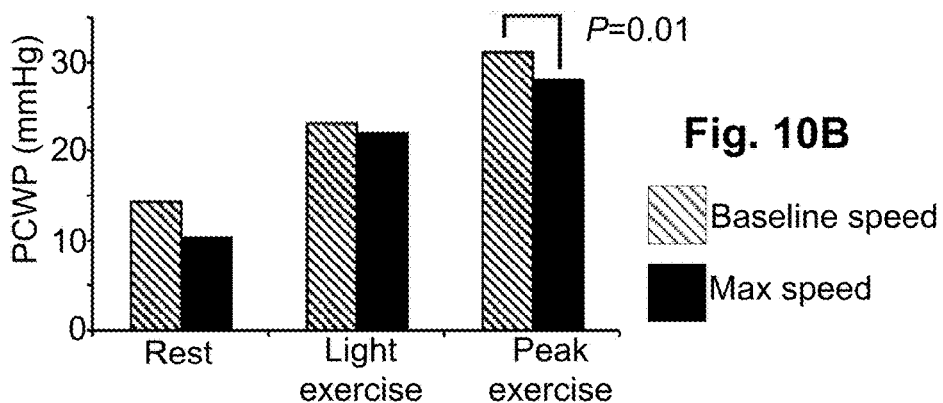
FIG. 10B is a graph showing an example of mean pulmonary capillary wedge pressure during rest, light exercise and peak exercise at baseline vs. maximum pump speed.

During peak exercise, pump flow was greater with maximum speed compared to baseline speed (7.7±0.6 L/min vs. 6.9±0.7 L/min, p=0.008), as shown in FIG. 10A, however CCO was significantly decreased (5.7±1.3 L/min vs. 6.6±1.5 L/min, p=0.01). Heart rate was significantly lower with exercise at maximum speed compared to baseline speed (112±25 bpm vs. 122±33 bpm, p=0.01). Exercise at maximum speed was also associated with a significant reduction in PCWP when compared to exercise at baseline speed (28±8 mmHg vs. 31±9 mmHg, p=0.01), as shown in FIG. 10B. MAP, RAP, MPAP and $SvO_2$ were not significantly different between the two speeds. LVEDD and LVESD remained unchanged. The aortic valve was opening in eight of the nine patients at baseline speed. At maximum speed, only six of these patients had their aortic valve opening and one patient had their valve intermittently opening. These findings are summarised in Tables 1 and 2 below.

In this regard, Table 1 shows heart rate, mean arterial pressure, central haemodynamic measures, mixed venous oxygen saturation and left ventricular dimensions during the rest, light and peak exercise performed at baseline and maximum pump speeds, whilst Table 2 shows changes in heart rate, mean arterial pressure, central haemodynamic measures and mixed venous oxygen saturation from baseline to maximum speed in individual patients performing peak exercise.

TABLE 1

|  |  | Rest Baseline Speed | Light Exercise | | | Peak Exercise | | |
| --- | --- | --- | --- | --- | --- | --- | --- | --- |
|  |  |  | Baseline Speed | Max. Speed | P | Baseline Speed | Max. Speed | p |
| Workload | (W) | 0 | 14± | 14± | 1.00 | 50± | 50± | 1.00 |
| HR | (bpm) | 83 ± 16 | 94± | 95± | 0.48 | 122± | 112± | <0.05 |
| MAP | (mmHg) | 84 ± 6 | 86± | 92± | <0.05 | 97± | 95± | 0.09 |
| Flow | (L/min) | 5.2 ± 0.8 | 5.8± | 6.8± | <0.01 | 6.9± | 7.7± | <0.01 |
| CCO | (L/min) | 4.8 ± 1.3 | 4.8± | 4.9± | 0.72 | 6.5± | 5.7± | <0.05 |
| RAP | (mmHg) | 7 ± 3 | 13± | 14± | 0.14 | 16± | 17± | 0.46 |
| MPAP | (mmHg) | 22 ± 7 | 31± | 31± | 0.55 | 40± | 38± | 0.09 |
| PCWP | (mmHg) | 15 ± 6 | 23± | 22± | 0.20 | 31± | 28± | <0.05 |
| SvO2 | (%) | 63 ± 4 | 45± | 44± | 0.67 | 26± | 28± | 0.23 |
| LVEDD | (mm) | 56 ± 13 | 51± | 53± | 0.46 | 53± | 50± | 0.36 |
| LVESD | (mm) | 49 ± 8 | 46± | 46± | 0.18 | 48± | 47± | 0.32 |

In table 1 the following abbreviations are used: HR, heart rate; MAP, mean arterial pressure; CCO, continuous cardiac output; RAP, right atrial pressure; MPAP, mean pulmonary arterial pressure; PCWP, pulmonary capillary wedge pressure; SvO2, mixed venous oxygen saturation; LVEDD, left ventricular end diastolic dimension; LVESD, left ventricular end systolic dimension.

TABLE 2

| No. | H | MA | Flo | CC | RA | MP | PC | Sv |
| --- | --- | --- | --- | --- | --- | --- | --- | --- |
| 1 | — | — | 0.1 | −0.9 | −1 | −3 | −2 | 0 |
| 2 | 1 | — | 1.0 | −0.8 | 0 | −1 | −4 | 9 |
| 3 | −3 | — | 1.1 | −1.4 | 0 | 0 | −2 | −3 |
| 4 | — | 4 | 0.8 | −1.0 | — | 3 | −8 | 4 |
| 5 | −3 | — | 0.7 | −0.5 | −1 | −2 | −2 | 4 |
| 6 | −5 | 0 | 0.7 | −1.3 | 0 | −2 | 0 | −6 |
| 7 | −3 | — | 0.6 | −0.7 | 2 | −4 | −7 | 5 |
| 8 | −2 | 0 | 1.1 | −1.3 | 0 | −1 | 1 | — |
| 9 | −6 | — | 1.3 | 0.0 | 2 | −3 | −4 | 4 |
| Me | −9 | — | 0.8 | −0.9 | 0 | −1 | −3 | 2 |
| SD | 1 | 4 | 0.4 | 0.5 | 1 | 2 | 3 | 5 |

Examination of lactate demonstrated that this increased from a resting average of 1.4±0.4 mmol/L to 4.3±2.0 mmol/L (p=0.02) post-exercise while BNP and LDH did not significantly change.

Multiple linear regression of diastolic dQ/dt with PCWP, heart rate, MAP and mean flow as predictor variables was performed with results shown in Table 3.

TABLE 3

|  | R2 | B coefficient | SE | Beta | p |
| --- | --- | --- | --- | --- | --- |
| PCWP | 0.75 | 0.23 | 0.034 | 0.70 | <0.001 |
| Heart Rate | 0.025 | 0.32 | 0.013 | 0.24 | 0.022 |
| MAP | — | — | — | 0.10 | 0.21 |
| Mean Flow | — | — | — | 0.11 | 0.12 |

Figure 11:
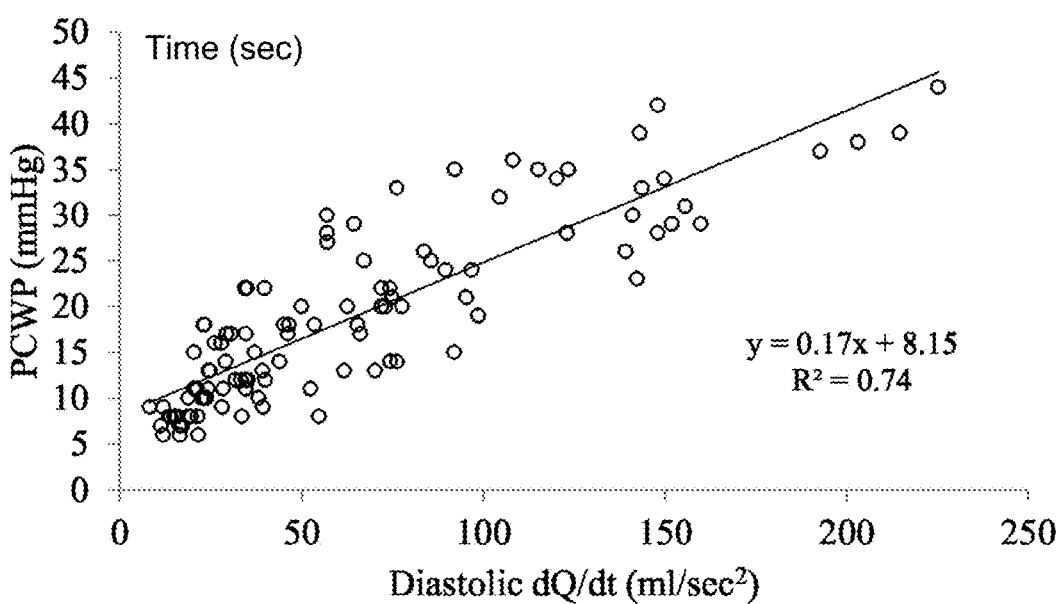
FIG. 11 is a graph of an example of the relationship between diastolic flow rate gradient and pulmonary capillary wedge pressure.

PCWP revealed that diastolic dQ/dt was a strong predictor ($R^2$=0.75, $\beta$=0.71, p<0.001). Heart rate accounted for only a small amount of the variance in PCWP ($R^2$=0.020, $\beta$=0.21, p=0.045), while MAP and mean flow did not significantly contribute to the model (p=0.46, p=0.99 respectively). The relationship between diastolic dQ/dt and PCWP is illustrated in FIG. 11. Furthermore, multiple linear regression of diastolic dQ/dt found that PCWP ($R^2$=0.75, $\beta$=0.70, p<0.001) and heart rate ($R^2$=0.025, $\beta$=0.24, p=0.022) were the only significant predicators.

Accordingly, the above described study identified that exercise resulted in an increase in the flow rate gradient, corresponding to an increase in ventricular filling pressure, and furthermore that increasing the pump speed of a cfL-VAD reduces the flow rate gradient and lower the ventricular filling pressure. This demonstrates the efficacy of the above described control protocol in which the pump speed is increased as the flow parameter value based on the flow rate gradient increases, allowing the VAD to accommodate increases in ventricular filling pressure that occurs during exercise. Additionally, speed was safely increased in all subjects and was not associated with any episodes of suction or significant reductions in ventricular dimensions.

It should be noted that whilst increased pump speed with exercise improved left-sided filling pressures, right heart pressures remained elevated. Mixed venous oxygen saturation did not improve with maximum pump speed despite the significant increase in pump flow.

Figure 12:
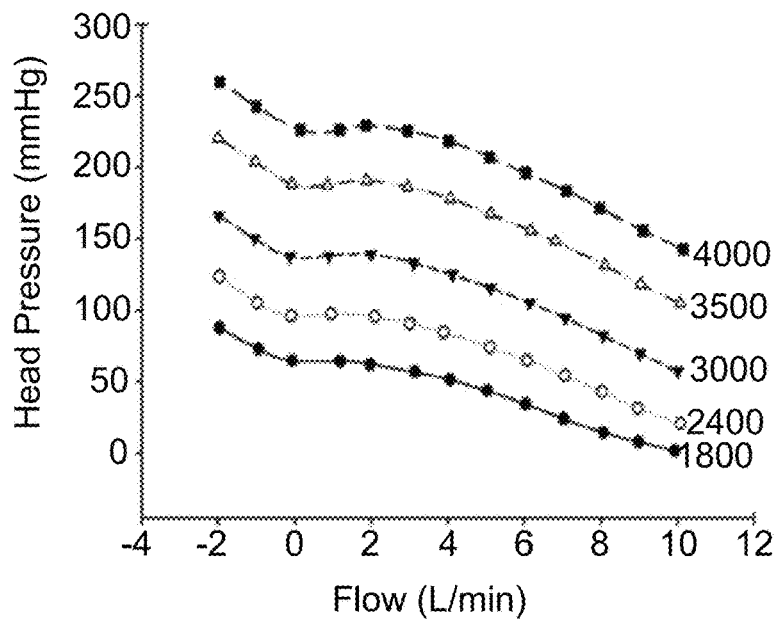
FIG. 12 is a graph of an example of the relationship between head pressure and flow rate at different pump speeds for the HeartWare VAD.

In any event, the study demonstrates an increase in flow with maximum pump speed over baseline speed during peak exercise. In this regard, it is understood that pump flow through a cfLVAD is influenced by a variety of factors, including pump speed and head pressure. In an LVAD, the head pressure corresponds to the difference between the aortic pressure and left ventricular pressure, with an increase in preload or a decrease in afterload resulting in an increase in flow. Thus, the spontaneous increase in pump flow from rest to exercise, regardless of speed adjustment, is largely attributed to an increase in venous return and preload. However, this does not account for the greater flows at higher pump speeds. As speed is increased, greater unloading of the left ventricle results in reduced preload and a higher head pressure, yet pump flow remains increased. This can be explained by FIG. 12 which illustrates the relationship between head pressure and flow at different pump speeds for the HeartWare HVAD. Higher pump speeds are able to generate the same amount of flow at substantially greater head pressures. Additionally the H-Q curve for the HeartWare HVAD is relatively flat which means that large fluctuations in flow occur for small changes in head pressure. Changes in pressure caused by native heart contractions therefore result in remarkably pulsatile flow through the HVAD, despite the classification of the pump as a cfLVAD.

It should be noted that although increased heart rate has a role in the augmentation of pump flow during exercise at fixed speed, the increase in flow seen in this study cannot be attributed to an increase in heart rate. The increased flow at maximum pump speed compared to baseline pump speed did not correspond with parallel changes in heart rate. Heart rate also remained unchanged during light exercise between baseline and maximum pump speed, despite increased flow at maximum speed.

Figure 13:
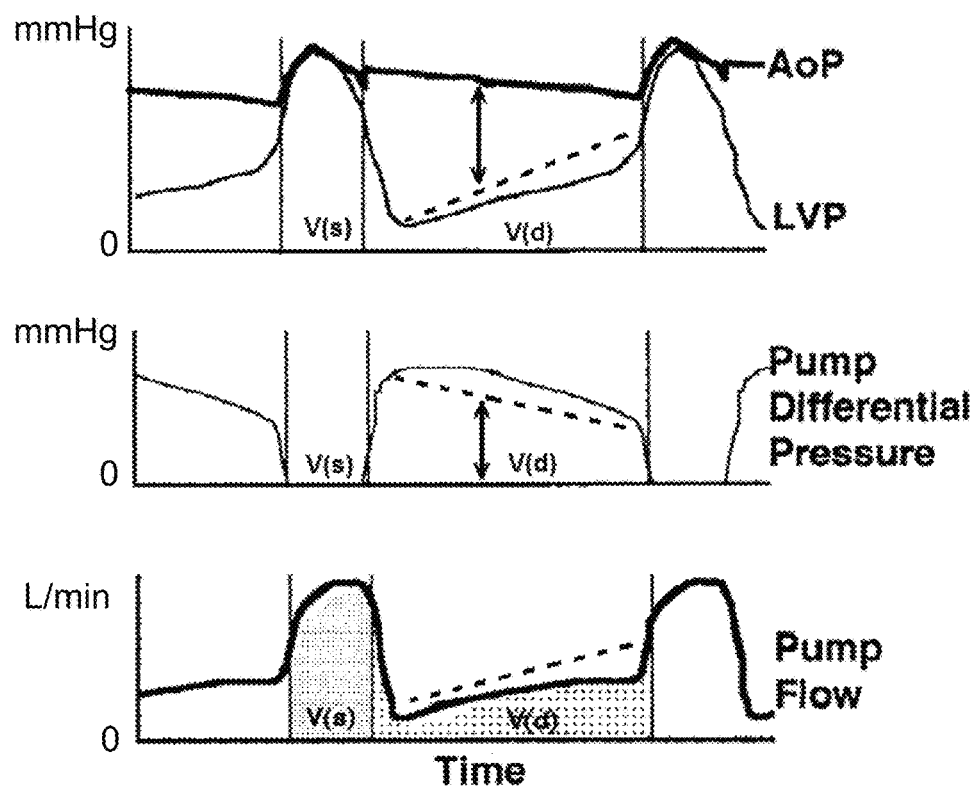
FIG. 13 shows graphs of examples of the relationships between blood pressure, pump pressure and pump flow.

Flow remained greater at maximum speed, despite the lesser heart rate, because increased pump speed confers a higher average minimum and, to a smaller extent, a higher average maximum flow as shown in FIG. 13. This diminishes the importance of the flow augmenting effect of systolic sparing at higher heart rates.

Though increased pump speed significantly improved PCWP and hence ventricular filling pressure at peak exercise, there were no significant reductions in right heart pressure. Despite this, MPAP was reduced in the majority of patients.

Thus, the diastolic flow rate gradient dQ/dt correlates with PCWP, which in turn provides an estimate of ventricular filling pressure and in particular left ventricular end-diastolic pressure. This is evident from the relationship between pump differential pressure and flow shown in FIG. 13, in which pump differential pressure equates to the difference between aortic pressure and left ventricular pressure. As left ventricular pressure and PCWP increase, pump differential pressure decreases. Given the inverse relationship between pump differential pressure and pump flow, this should result in an increase in the gradient of flow during diastole, and hence diastolic flow rate gradient dQ/dt.

Further investigations were performed using a mock-loop study in which a VAD was incorporated into a mock cardiac circulation loop and a range of different haemodynamic states simulated. A number of these results will now be described. For the purpose of these experiments and given the experimental set-up, left atrial pressure (LAP) was controlled, with this being used as an approximation for the ventricular filling pressure, which is reasonable given the mock-circulation loop is simulating an idealised circulatory system.

Figure 14:
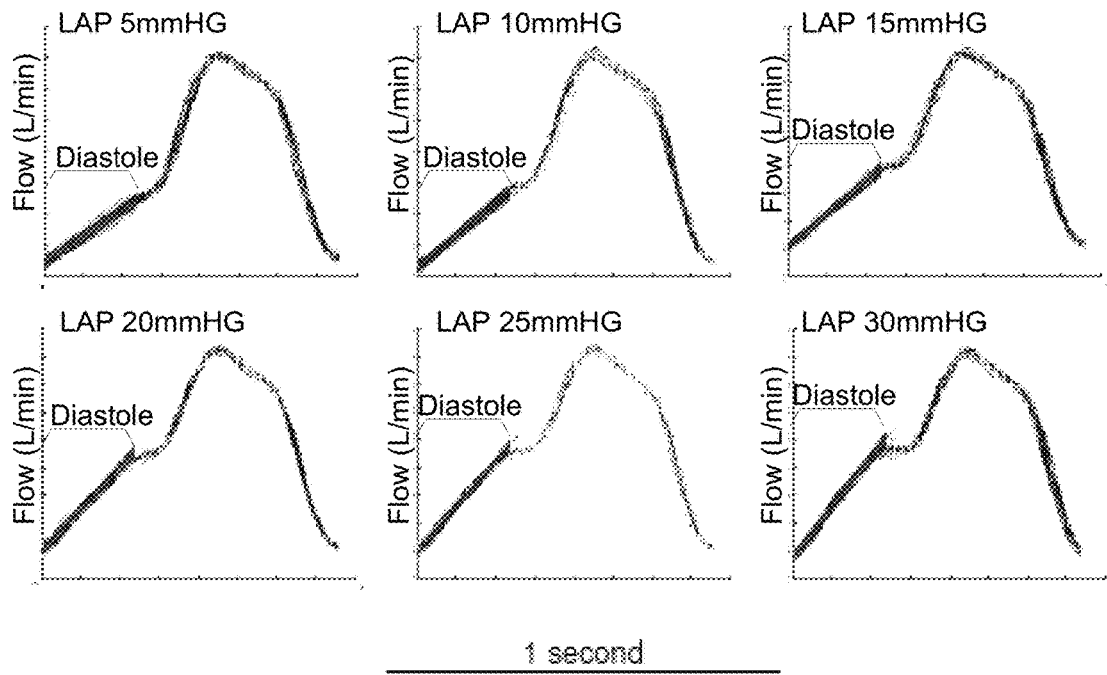
FIG. 14 shows graphs of example flow against time curves in a mock circulation loop for different simulated atrial pressures.

In a first experiment, a number of different LAPs were simulated, with resulting flow against time curves being shown in FIG. 14, with the diastolic flow rate Q being highlighted. This clearly shows that as LAP and hence ventricular filling pressure increases, there is a corresponding increase in the flow rate gradient dQ/dt.

Figure 15A:
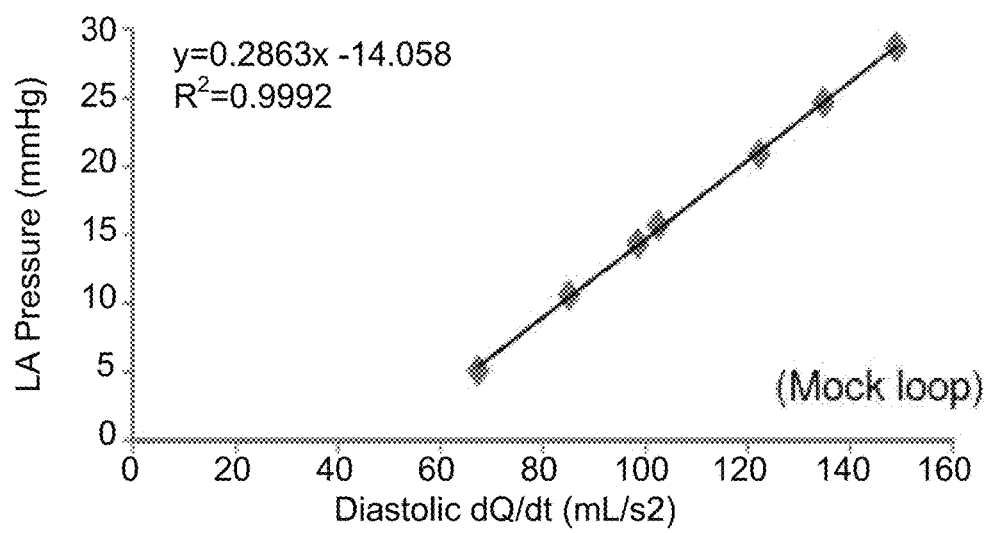
FIGS. 15A and 15B are graphs showing examples of the relationship between left atrial pressure and flow rate gradient during diastole for different mock circulation loop configurations.
Figure 15B:
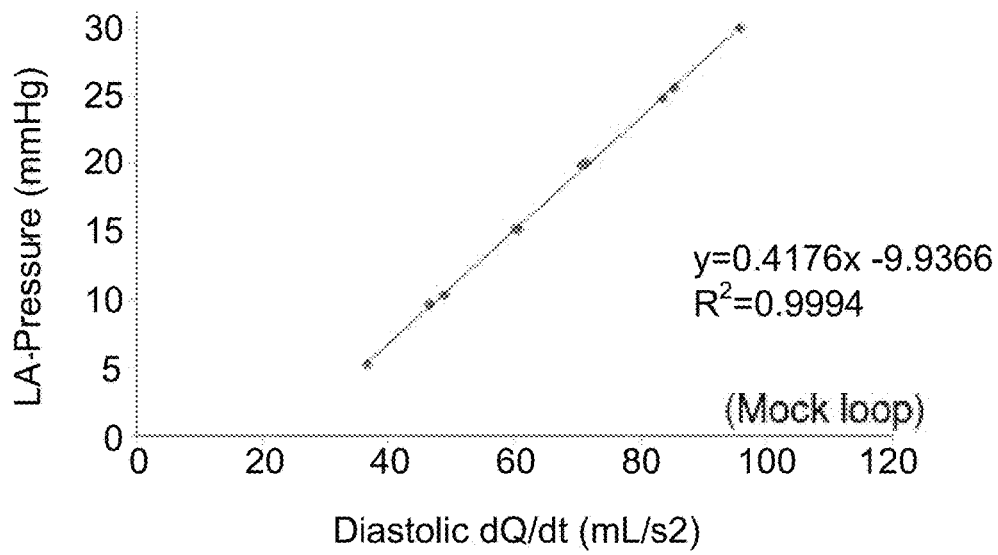

Examples of the correlation between LAP and flow rate gradient dQ/dt for two different haemodynamic states are shown in FIGS. 15A and 15B, with each case demonstrating a high degree of correlation (R=0.9992 and R=0.9994 respectively).

Figure 16:
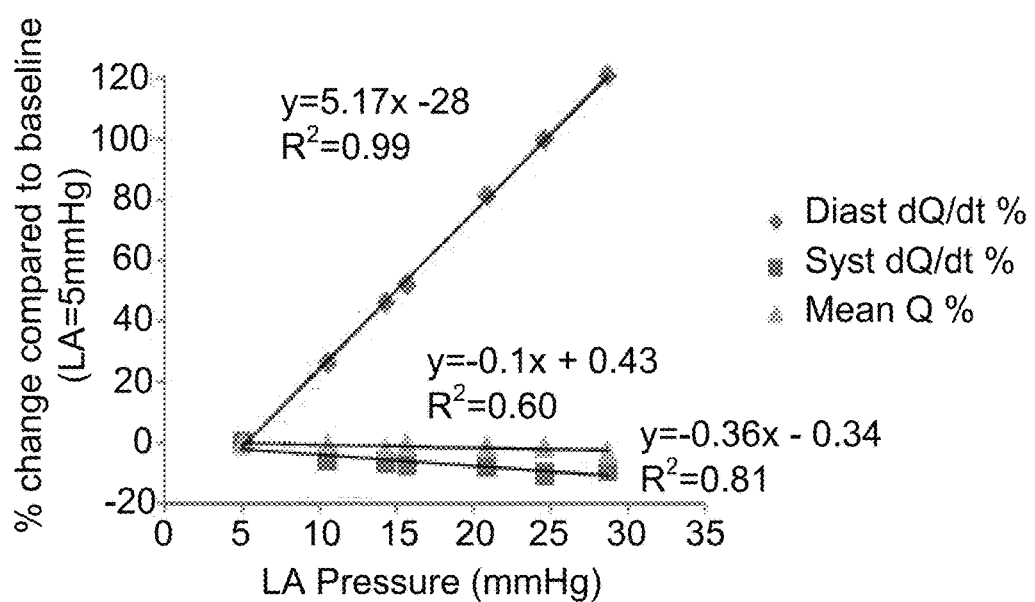
FIG. 16 is a graph of examples of changes in flow rates of different portions of the cardiac cycle for different atrial pressures simulated in a mock circulation loop.

FIG. 16 shows how variation in LAP leads to a change in the diastolic flow rate gradient, the systolic flow rate gradient and mean flow rate, again demonstrating good correlation with the diastolic flow rate gradient.

Figure 17:
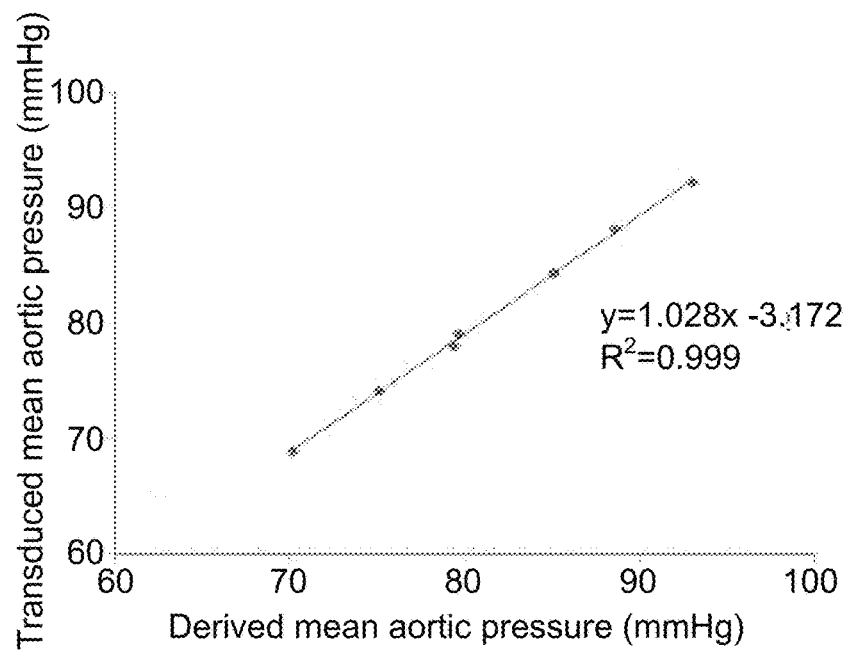
FIG. 17 is a graph of an example of the correlation of derived mean aortic pressure with measured aortic pressure in a mock circulation loop.

FIG. 17 is a graph showing the measured MAP compared to a derived MAP determined from the flow parameter value using equation (6) above, again demonstrating a high degree of correlation.

Figure 18A:
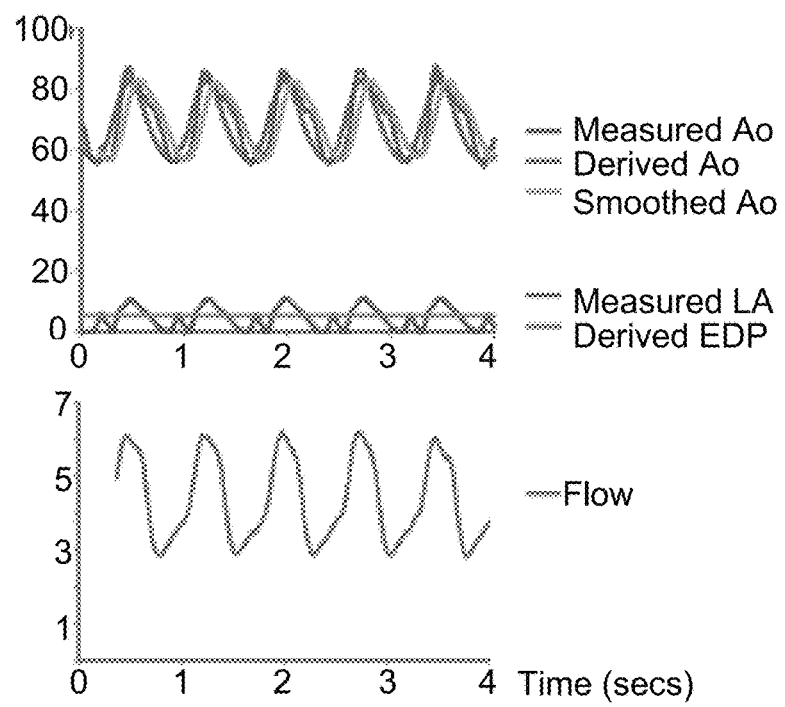
FIGS. 18A to 18D show graphs of measured and derived blood pressure parameter values over a number of cardiac cycles in a mock circulation loop; and, FIG. 19 is an example of a representation of blood pressure parameter values.
Figure 18B:
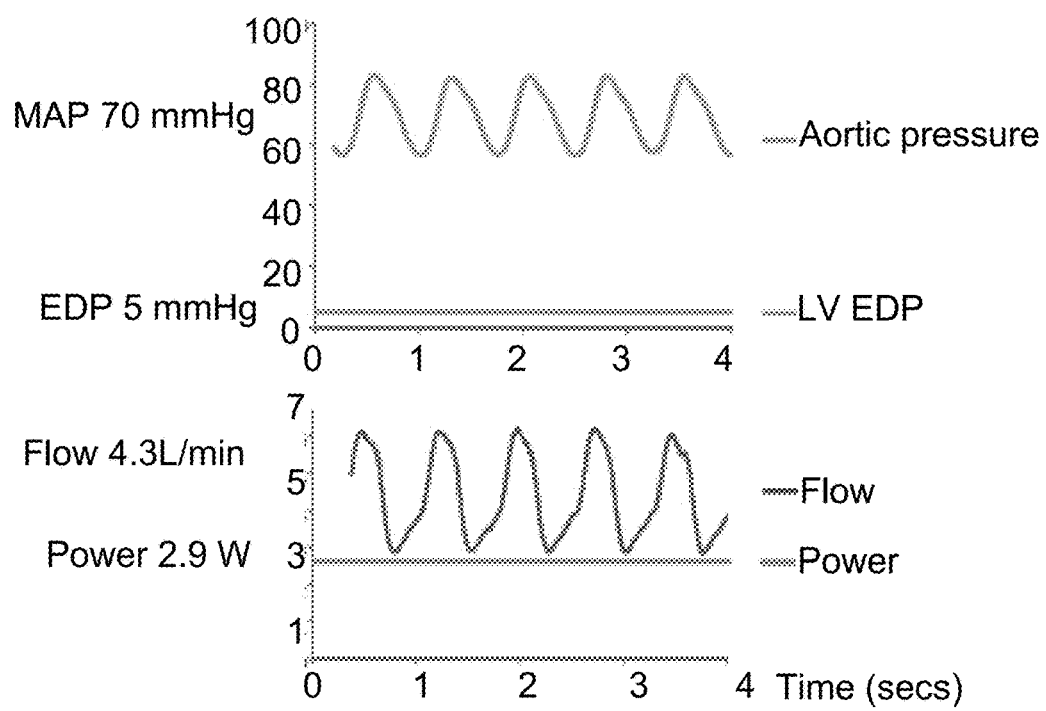
Figure 18C:
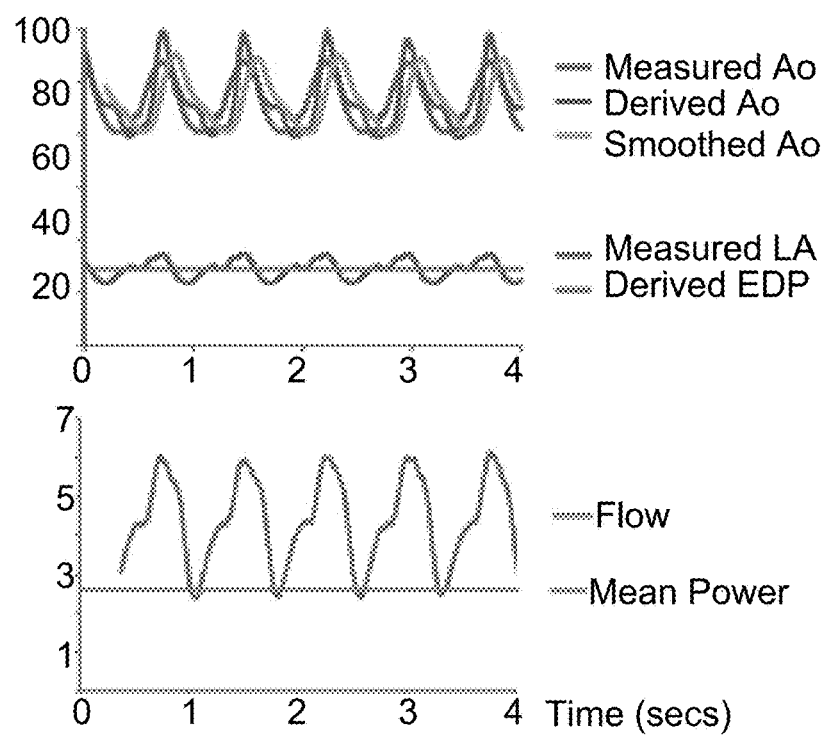
Figure 18D:
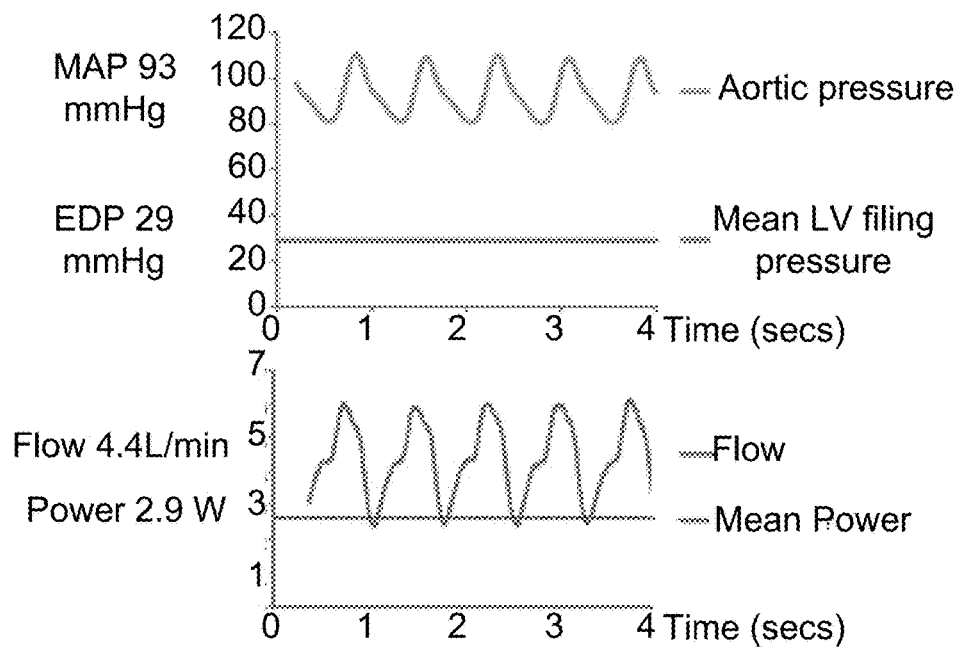

FIGS. 18A to 18D show graphs of measured and derived blood pressure parameter values over a number of cardiac cycles in the mock circulation loop. FIGS. 18A and 18C include comparison of measured, derived and smoothed aortic pressure, as well as a comparison of measured LAP and derived EDP corresponding to the ventricular filling pressure, again showing good correlation, whilst FIGS. 18B and 18D show corresponding power, flow and EDP used in calculating the MAP.

Accordingly the above described techniques can therefore be used to determine a flow parameter value, and in particular a flow rate gradient during diastole, which can in turn be used to control a VAD and determine blood pressure parameter values including a ventricular filling pressure, and in particular an EDP, with this in turn being used in conjunction with VAD operating parameters to calculate a MAP.

Figure 19:
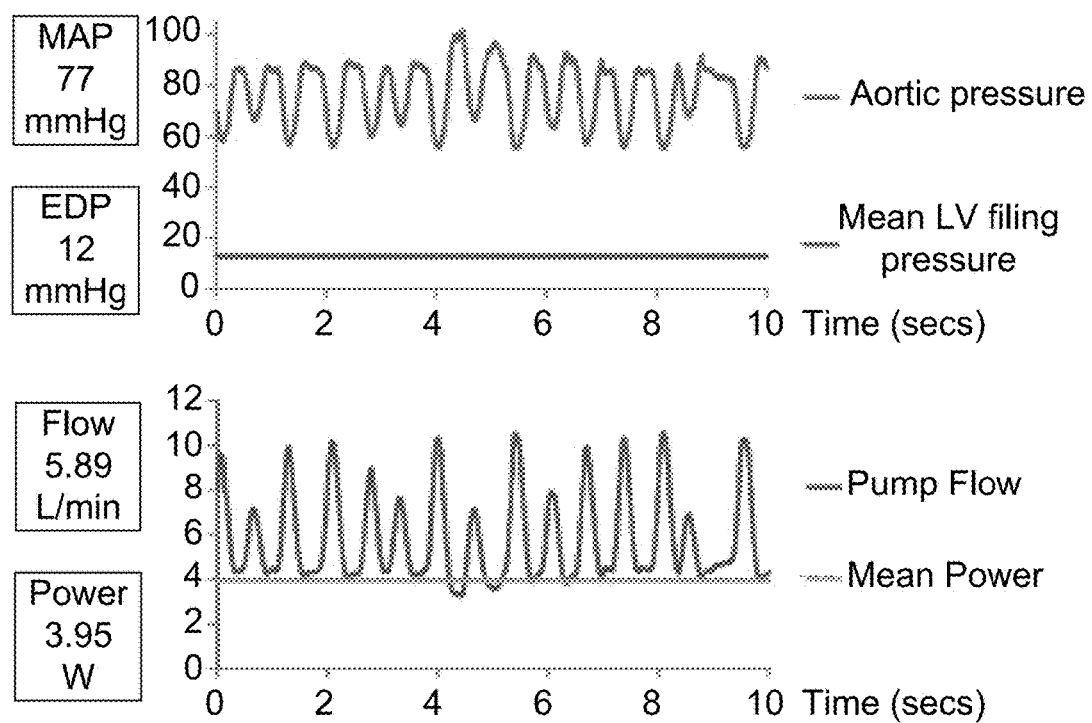

It will therefore be appreciated that in practice, when a patient is fitted with a VAD, this allows a ventricular EDP and MAP to be displayed on a heart monitor or the like, as shown for example in FIG. 19. In addition, the flow parameter value and/or pressure parameter value can also be used to control the VAD and in particular increase the VAD speed in response to an increase in flow rate gradient or blood pressure parameter, thereby increasing flow through the VAD and returning the ventricular filling pressure to a normal level.

As mentioned above, the use of dQ/dt, and in particular the use of the time period between minimum flow and half maximum flow is not intended to be limiting when calculating the gradient. By way of illustration, a comparative analysis was performed between dQ/dt and ndQ/dt.

In this regard, ndQdt encompasses only an early portion of the diastolic flow, specifically between minimum flow and half maximum flow. Examination of data collected from a mock circulation loop shows that certain diastolic flow portions exhibit a plateau before the systolic portion, thus reducing the gradient measured using dQdt. Secondly, the measure dQdt infrequently included parts of the systolic flow waveform, thus markedly increasing the gradient measured. Examples of this are shown in FIGS. 20A to 20C.

Figure 20A:
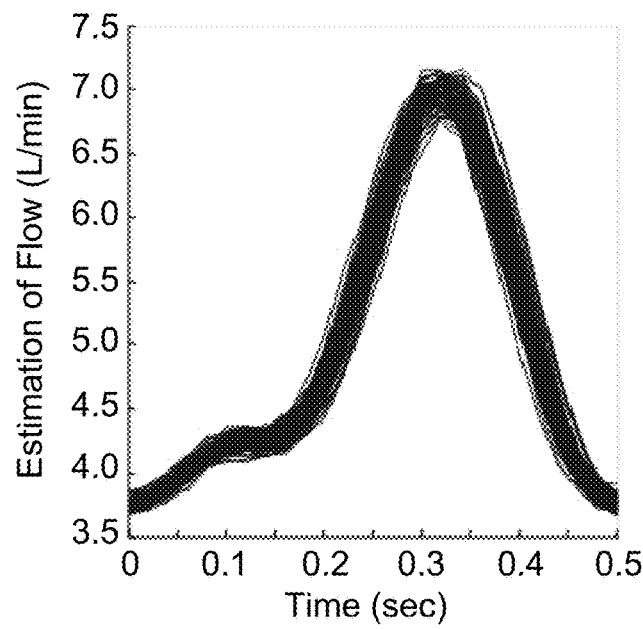
FIG. 20A is a graph of an example of flow data showing a plateau in flow at the end of diastole.
Figure 20B:
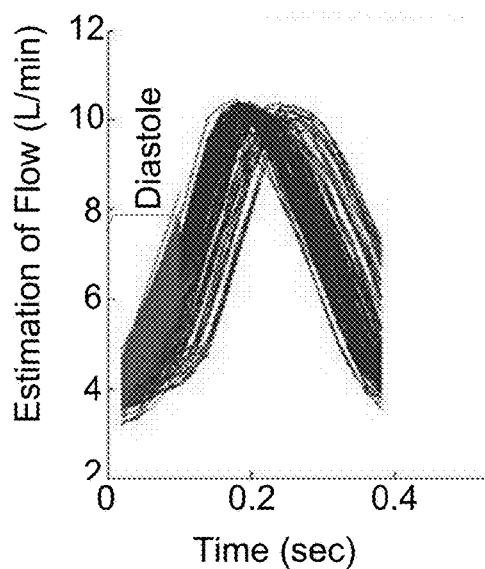
FIG. 20B is a graph of an example of flow data showing example gradients for a first time period; and, FIG. 20C is a graph of an example of flow data showing example gradients for a second time period.
Figure 20C:
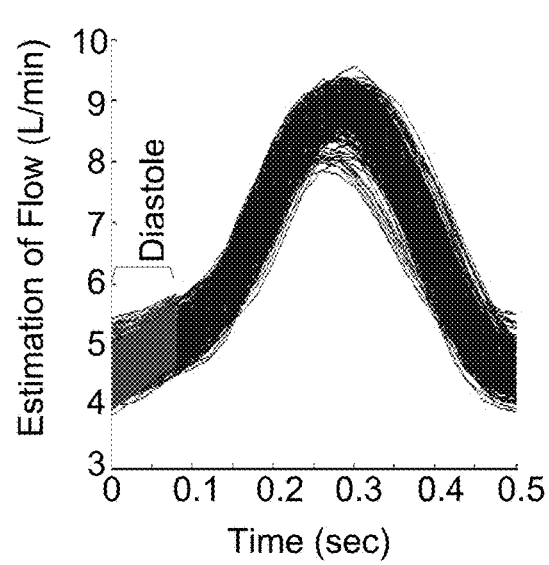

In this regard, a plateau in flow rate towards the end of diastole is shown in FIG. 20A. The use of a first time period, corresponding to the point of lowest flow to half flow, and resulting inclusion of systole within the dQ/dt calculation of gradient is shown in FIG. 20B, highlighting significant variation in gradient values. In comparison, in the example of FIG. 20C, a second shorter time period is used to calculate ndQ/dt, thereby exclude any plateau and systole, leading to greater consistency in gradient values.

Measured data demonstrates ndQ/dt is highly correlated with surrogate measurements of preload, LAP and PCWP in both a mock circulation loop and cfLVAD patients respectively. Additionally, results show ndQ/dt to be very robust in the mock circulation loop, with changes in haematocrit, AoP and HR having no effect on the efficacy of ndQ/dt as a measure of pressure. Changes in LVAD speed also have a negligible impact, individually accounting for only 0.4% of the variance in ndQ/dt. This finding was confirmed in patient studies where HR and LVAD speed were not found to influence ndQ/dt, meaning that the measure ndQ/dt can be used in a wide range of clinical scenarios. In contrast, dQ/dt whilst accurate in most cases, is influenced by HR, possibly due to portions of systolic waveform being included at higher HR, thus artificially increasing dQ/dt.

Nevertheless both ndQ/dt and dQ/dt demonstrated a strong ability to detect elevated or reduced preload, with an AUC (Area Under Curve) over 0.97 in the mock circulation loop using ndQ/dt and AUC over 0.85 in vivo using either ndQ/dt or dQ/dt. This highlights that a range of different time periods for gradient measurements could be used and that the time periods for measuring ndQ/dt or dQ/dt, whilst useful, should not be considered as restrictive.

Thus, it will also be appreciated that the use of a half or quarter of the maximum flow rate as the end of diastole, for the purpose of determining the gradient, is not intended to be limiting and any suitable end point could be used. Additionally, the end point used could be varied dynamically, for example based on other parameters, such as the heart rate, or the like.

Having a robust, continuous marker of elevated preload allows clinicians to determine the potential need to offload the left ventricle, either through increasing pump speed or by using diuretics, without the need for invasive right heart catheterization. Furthermore, a warning that preload was reduced could assist clinicians in reducing the risk of ventricular suction and over-pumping and could be integrated into physiological pump controllers.

In any event, the above described techniques therefore allow for successful estimation of LAP and PCWP, as surrogates for preload, in both in vitro and in vivo settings from HVAD flow waveform analysis. This also allows for the estimation of mean arterial pressure and head pressure using only HVAD pump parameters, which in turn allows for continuous non-invasive estimation of blood pressure in patients with HVADs.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. Apparatus for use with a ventricular assist device that is assisting cardiac function of a biological subject, the apparatus including an electronic processing device that:
   a) determines a flow rate of blood through the ventricular assist device;
   b) analyses the flow rate to determine a flow parameter value, wherein the flow parameter value is indicative of a flow rate gradient during diastole and is determined by:
      i) determining the flow rate over at least one cardiac cycle;
      ii) analysing the flow rate to identify a period of the cardiac cycle corresponding to diastole;
      iii) determining the flow rate gradient during the diastole period; and,
      iv) determining the flow rate parameter value using the flow rate gradient; and,
   c) uses the flow parameter value to control the ventricular assist device.

2. Apparatus according to claim 1, wherein the electronic processing device:
   a) compares a parameter value to at least one threshold, the parameter value being at least one of the flow parameter value and a blood pressure parameter value; and,
   b) in response to results of the comparison, at least one of:
      i) selectively adjusts blood flow through the ventricular assist device; and
      ii) selectively generates a notification.

3. Apparatus according to claim 2, wherein the threshold is at least one of:
   a) indicative of a nominal range;
   b) determined based on a parameter value determined from a sample population; and,
   c) at least in part based on a parameter value previously determined for the subject.

4. Apparatus according to claim 1, wherein the ventricular assist device includes a rotating impeller, and wherein the electronic processing device controls blood flow through the ventricular assist device by causing a rate of rotation of the impeller to be adjusted.

5. Apparatus according to claim 1, wherein the electronic processing device:
   a) analyses the flow rate over a plurality of cardiac cycles;
   b) determines a mean flow rate gradient during diastole; and,
   c) determines the flow rate parameter value using a mean flow rate gradient.

6. Apparatus according to claim 5, wherein the electronic processing device:
   a) calculates flow rate maxima and minima for each of the plurality of cardiac cycles; and,
   b) selectively excludes a cardiac cycle based on at least one of the respective flow rate maxima and minima of the cardiac cycle.

7. Apparatus according to claim 6, wherein the electronic processing device selectively excludes cardiac cycles corresponding to suction events.

8. Apparatus according to claim 5, wherein the electronic processing device:
   a) calculates flow rate maxima and minima for each of the plurality of cardiac cycles; and,
   b) determines a period of the cardiac cycle corresponding to diastole using the flow rate maxima and minima.

9. Apparatus according to claim 8, wherein the electronic processing device determines diastole as a period of the cardiac cycle from the flow rate minima to proportion of the flow rate maxima.

10. Apparatus according to claim 9, wherein the proportion of the flow rate maxima is at least one of:
    a) half of the flow rate maxima; and,
    b) quarter of the flow rate maxima.

11. Apparatus according to claim 1, wherein the electronic processing device analyses the flow rate using waveform analysis.

12. Apparatus according to claim 1, wherein the electronic processing device at least one of:
    a) records the flow parameter value;
    b) displays a representation of the flow parameter value;
    c) records a blood pressure parameter value; and,
    d) displays a representation of the blood pressure parameter value.

13. Apparatus according to claim 1, wherein the at least one blood pressure parameter value is at least partially indicative of at least one of:
    a) an intra-cardiac pressure;
    b) an atrial pressure;
    c) a ventricular filling pressure;
    d) a pulmonary capillary wedge pressure;
    e) a ventricular end diastole pressure; and,
    f) a mean arterial pressure.

14. Apparatus according to claim 1, wherein the electronic processing device:
    a) calculates a ventricular filling pressure using the flow parameter value;
    b) determines a ventricular assist device power usage; and,
    c) calculates a mean arterial pressure using the ventricular filling pressure and the ventricular assist device power usage.

15. Apparatus according to claim 1, wherein the electronic processing device is at least one of:
   a) at least part of a ventricular assist device controller; and,
   b) coupled to a ventricular assist device controller.

16. Apparatus according to claim 1, wherein the electronic processing device determines the blood flow rate at least one of:
   a) in accordance with signals received from a sensor;
   b) by receiving flow rate data from a ventricular assist device controller; and,
   c) by calculating a flow rate based on rotation of a ventricular assist device impeller.

17. A method for use with a ventricular assist device that is assisting cardiac function of a biological subject, the method including:
   a) determining a flow rate of blood through the ventricular assist device;
   b) analysing the flow rate to determine a flow parameter value, wherein the flow parameter value is indicative of a flow rate gradient during diastole and is determined by:
      i) determining the flow rate over at least one cardiac cycle;
      ii) analysing the flow rate to identify a period of the cardiac cycle corresponding to diastole;
      iii) determining the flow rate gradient during the diastole period; and,
      iv) determining the flow rate parameter value using the flow rate gradient; and,
   c) using the flow parameter value to control the ventricular assist device.

18. Apparatus for use when assisting cardiac function of a biological subject, the apparatus including:
   a) a ventricular assist device: and,
   b) an electronic processing device that:
      i) measures a flow rate of blood by the ventricular assist device;
   c) analyses the flow rate to determine a flow parameter value, wherein the flow parameter value is indicative of a flow rate gradient during diastole and is determined by:
      i) determining the flow rate over at least one cardiac cycle;
      ii) analysing the flow rate to identify a period of the cardiac cycle corresponding to diastole;
      iii) determining the flow rate gradient during the diastole period; and,
      iv) determining the flow rate parameter value using the flow rate gradient; and,
   d) uses the flow parameter value to derive at least one blood pressure parameter value at least partially indicative of a blood pressure in the biological subject.

19. A method for use when assisting cardiac function of a biological subject, the method including:
   a) using a ventricular assist device to assist cardiac function of the biological subject;
   b) using an electronic processing device to:
      i) measure a flow rate of blood by the ventricular assist device;
   c) analyse the flow rate to determine a flow parameter value, wherein the flow parameter value is indicative of a flow rate gradient during diastole and is determined by:
      i) determining the flow rate over at least one cardiac cycle;
      ii) analysing the flow rate to identify a period of the cardiac cycle corresponding to diastole;
      iii) determining the flow rate gradient during the diastole period; and,
      iv) determining the flow rate parameter value using the flow rate gradient; and,
   d) use the flow parameter value to control the ventricular assist device.

20. Apparatus including:
   a) a ventricular assist device that is assisting cardiac function of a biological subject; and,
   b) an electronic processing device that:
      i) determines a flow rate of blood through the ventricular assist device;
      ii) analyses the flow rate to determine a flow parameter value, wherein the flow parameter value is indicative of a flow rate gradient during diastole and is determined by:
         1) determining the flow rate over at least one cardiac cycle;
         2) analysing the flow rate to identify a period of the cardiac cycle corresponding to diastole;
         3) determining the flow rate gradient during the diastole period; and,
         4) determining the flow rate parameter value using the flow rate gradient; and,
      iii) uses the flow parameter value to control the ventricular assist device.

* * * * *